US008604072B2

(12) United States Patent
Anderson et al.

(10) Patent No.: US 8,604,072 B2
(45) Date of Patent: Dec. 10, 2013

(54) TREATMENT USING DANTROLENE

(75) Inventors: David Anderson, Ashland, VA (US);
Benjamin G. Cameransi, Jr.,
Georgetown, SC (US); Vincent M. Conklin, Richmond, VA (US)

(73) Assignee: Lyotropic Therapeutics, Inc., Ashland, VA (US)

( * ) Notice: Subject to any disclaimer, the term of this patent is extended or adjusted under 35 U.S.C. 154(b) by 37 days.

(21) Appl. No.: 13/353,480

(22) Filed: Jan. 19, 2012

(65) Prior Publication Data

US 2012/0121663 A1   May 17, 2012

Related U.S. Application Data

(63) Continuation of application No. 12/717,588, filed on Mar. 4, 2010, now Pat. No. 8,110,225, which is a continuation of application No. 10/788,413, filed on Mar. 1, 2004, now Pat. No. 7,758,890, which is a continuation-in-part of application No. 10/170,236, filed on Jun. 13, 2002, now abandoned.

(60) Provisional application No. 60/539,324, filed on Jan. 28, 2004, provisional application No. 60/451,249, filed on Mar. 4, 2003, provisional application No. 60/300,482, filed on Jun. 23, 2001.

(51) Int. Cl.
*A61K 31/415* (2006.01)
*A61K 9/14* (2006.01)
*A61K 9/00* (2006.01)

(52) U.S. Cl.
USPC ............................ 514/389; 424/489; 424/400

(58) Field of Classification Search
USPC .................................. 424/489, 400; 514/389
See application file for complete search history.

(56) References Cited

U.S. PATENT DOCUMENTS

| | | | |
|---|---|---|---|
| 4,137,402 A | 1/1979 | White | |
| 4,543,359 A | 9/1985 | Ellis et al. | |
| 4,725,442 A | 2/1988 | Haynes | |
| 4,952,402 A | 8/1990 | Sparks et al. | |
| 5,091,188 A | 2/1992 | Haynes | |
| 5,145,684 A | 9/1992 | Liversidge et al. | |
| 5,298,262 A | 3/1994 | Na et al. | |
| 5,302,401 A | 4/1994 | Liversidge et al. | |
| 5,346,702 A | 9/1994 | Na et al. | |
| 5,352,459 A | 10/1994 | Hollister et al. | |
| 5,429,824 A | 7/1995 | June | |
| 5,470,583 A | 11/1995 | Na et al. | |
| 5,503,723 A | 4/1996 | Ruddy | |
| 5,510,118 A | 4/1996 | Bosch et al. | 424/489 |
| 5,518,187 A | 5/1996 | Bruno et al. | |
| 5,534,270 A | 7/1996 | De Castro | |
| 5,560,931 A | 10/1996 | Eickhoff et al. | |
| 5,560,932 A | 10/1996 | Bagchi et al. | |
| 5,565,188 A | 10/1996 | Wong et al. | |
| 5,569,448 A | 10/1996 | Wong et al. | |
| 5,571,536 A | 11/1996 | Eickhoff et al. | |
| 5,573,783 A | 11/1996 | Desieno et al. | |
| 5,585,108 A | 12/1996 | Ruddy et al. | |
| 5,587,143 A | 12/1996 | Wong | |
| 5,622,938 A | 4/1997 | Wong | |
| 5,662,883 A | 9/1997 | Bagchi et al. | |
| 5,665,331 A | 9/1997 | Bagchi et al. | |
| 5,705,194 A | 1/1998 | Wong et al. | |
| 5,716,642 A | 2/1998 | Bagchi et al. | |
| 5,718,388 A | 2/1998 | Czekai et al. | |
| 5,834,025 A | 11/1998 | De Garavilla et al. | |
| 5,862,999 A | 1/1999 | Czekai et al. | |
| 5,936,030 A | 8/1999 | Nicholas et al. | |
| 6,267,989 B1 | 7/2001 | Liversidge et al. | |
| 6,270,806 B1 | 8/2001 | Liversidge et al. | |
| 6,294,192 B1 | 9/2001 | Patel et al. | 424/451 |
| 6,375,986 B1 | 4/2002 | Ryde et al. | |
| 6,428,814 B1 | 8/2002 | Bosch et al. | |
| 6,432,381 B2 | 8/2002 | Liversidge et al. | |
| 6,462,066 B2 | 10/2002 | Mangat et al. | |
| 6,495,164 B1 | 12/2002 | Ramstack et al. | 424/489 |
| 6,582,285 B2 | 6/2003 | Czekai et al. | |
| 6,592,903 B2 | 7/2003 | Ryde et al. | |

(Continued)

FOREIGN PATENT DOCUMENTS

| | | |
|---|---|---|
| JP | 53-20413 | 2/1978 |
| WO | WO 94/05287 | 3/1994 |

(Continued)

OTHER PUBLICATIONS

Larach et al., *Cardiac Arrest and Deaths Associated with Malignant Hyperthermia in North America from 1987 to 2006*, Anesthesiology 2008; 108: 603-611.

Lecithin, entry in Wikipedia online encyclopedia, downloaded Jul. 24, 2009 from http://en.wikipedia.org/wiki/Lecithin.

S. Becker, et al., 2008. "Comparison of Systemic Effects of 3,4-Methylenedioxymethamphetamine, of Ryanodex Therapy and Uncoupling Protein 3 Expression in Malignant Hyperthermia Susceptible and Normal Swine". Malignant Hyperthermia Assn. of the United States, http://medical.mhaus.org/index.cfm/fuseaction/Content.Display/PagePK/DanielMassikAward2008.cfm.

(Continued)

*Primary Examiner* — Shengjun Wang
(74) *Attorney, Agent, or Firm* — Lucas & Mercanti, LLP

(57) ABSTRACT

Provided are low-volume, safe for injection formulations of dantrolene yielding significant advantages over the currently approved and marketed dantrolene for malignant hyperthermia (MH) threatening anesthetic crisis. Once dantrolene can be made immediately available to patients triggered of MH, the anesthesiologist will be able to focus exclusively on the management of the patient's physiologic status in this complex and evolving crisis, not on the laborious and time consuming reconstitution process of the rescue agent. The low volume, safe for injection formulations of dantrolene have significant advantages over currently used approaches to the prevention and treatment of pumphead, and other neurological, cognitive and motor dysfunction incident to iatrogenically or trauma induced situations of altered blood flow, including those incurred during surgical procedures involving CPB or related procedures, as well as those incurred during non-normothermic episodes caused iatrogenically or by disease.

19 Claims, No Drawings

(56) References Cited

U.S. PATENT DOCUMENTS

| | | |
|---|---|---|
| 6,742,734 B2 | 6/2004 | Reed et al. |
| 6,976,647 B2 | 12/2005 | Reed et al. |
| 7,198,795 B2 | 4/2007 | Cooper et al. |
| 7,288,267 B2 | 10/2007 | Bosch et al. |
| 7,459,283 B2 | 12/2008 | Wertz et al. |
| 2003/0054042 A1 | 3/2003 | Liversidge et al. |
| 2003/0087308 A1 | 5/2003 | Lindner et al. |
| 2004/0026546 A1 | 2/2004 | Czekai |
| 2004/0105778 A1 | 6/2004 | Lee et al. |
| 2004/0105889 A1 | 6/2004 | Ryde et al. |
| 2004/0173696 A1 | 9/2004 | Cunningham et al. |
| 2004/0176123 A1 | 9/2004 | Chin et al. |
| 2004/0195413 A1 | 10/2004 | Reed et al. |
| 2004/0258757 A1 | 12/2004 | Bosch et al. |
| 2005/0031691 A1 | 2/2005 | McGurk et al. |

FOREIGN PATENT DOCUMENTS

| | | |
|---|---|---|
| WO | WO 02/43696 | 6/2002 |
| WO | WO 03/000057 | 1/2003 |
| WO | WO 2004/105809 | 12/2004 |
| WO | WO 2005/044234 | 5/2005 |

OTHER PUBLICATIONS

Krause, et al., 2004. "Dantrolene—A review of its pharmacology, therapeutic use and new developments". Anaesthesia, 59: 364-373.

Gerbershagen, et al., 2007. "Comparison of Therapeutic Effectiveness of Dantrolene and Ryanodex in Porcine Malignant Hyperthermia". Anesthesiology, 107: A1922.

Schutte, et al., 2007. "Effects and Safety of the Novel Formulation Ryanodex in Malignant Hyperthemia Normal Swine", Anesthesiology, 107: A1928.

Brandom, et al., 2002. "Reassessment of the Safety and Efficacy of Dantrolene". Anesthesiology, 96: A1199.

Harrison, et al., 2006. "Use of Cognitive Aids in a Simulated Anesthetic Crisis". Anesthesia & Analgesics, vol. 103. No. 3, pp. 551-556.

Karan, et al., 1996. "Intravenous Lecithin-Coated Microcrystals of Dantrolene Are Effective in the Treatment of Malignant Hyperthermia: An Investigation in Rats, Dogs and Swine". Anesth Analg, 82: 796-802.

Bouchama, et al., 2002. "Heat Stroke". N Engl J Med, 346:25 pp. 1978-1988.

"Injectable Dispersed Systems: Formulation, Processing and Performance"by Diane J. Burgess, ed. Informa Healthcare, 1, edition (May 23, 2005) ISBN-10 0849336996, p. 79.

Frandsen et al. "Dantrolene Prevents Glutamate Cytotoxicity and Ca2+ Release from Intracellualr Stores in Cultured Cerebral Cortical Neurons" Journal of Neurochemistry, pp. 1075-1078; 1991.

Frandsen et al. "Dantrolene Prevents Glutamate Cytotoxicity and Ca2+ Release from Intracellualr Stores in Cultured Cerebral Cortical Neurons" (Abstract 1075-8); 1991.

Zhang et al. "Dantrolene protects against ischemic, delayed neuronal death in gerbil brain" Neuroscience Letters, 158, pp. 105-108; 1993.

Zhang et al. "Dantrolene protects against ischemic, delayed neuronal death in gerbil brain" Neuroscience Letters, 158, pp. 105-108; 1993 (Abstract) 158 (1): 105-8.

Niebauer et al. "Neuroprotective effects of early vs. late administration of dantrolene in experimental status epilepticus" Neuropharmacology 38, pp. 1343-1348; 1999.

Wei et al. "Dantrolene Is Cytoprotective in Two Models of Neuronal Cell Death" Journal of Neurochemistry, pp. 2390-2398 1996.

Wei et al. "Neuronal Apoptosis Induced by Pharmacological Concentrations of 3-Hydroxykynurenine: Characterization and Protection by Dantrolene and Bcl-2 Overexpression" Journal of Neurochemistry, pp. 81-90; 2000.

McDonald et al. "Seizures and Brain Injury in Neonatal Rats Induced bt 1 S, 3R-ACPD, a Metabotropic Glutamate Receptor Agonist" The Journal of Neuroscience, pp. 4445-4455; Oct. 1993.

TREATMENT USING DANTROLENE

CROSS REFERENCES TO RELATED APPLICATIONS

This application is a continuation of U.S. application Ser. No. 12/717,588 filed Mar. 4, 2010 (now U.S. Pat. No. 7,758,890), which is a continuation of U.S. application Ser. No. 10/788,413 filed Mar. 1, 2004, which claims the benefit of U.S. Provisional Application Ser. Nos. 60/539,324 filed Jan. 28, 2004 and 60/451,249 filed Mar. 4, 2003, and which is a continuation-in-part of U.S. application Ser. No. 10/170,236 filed Jun. 13, 2002 (abandoned), which claims the benefit of U.S. Provisional Application Ser. No. 60/300,482 filed Jun. 23, 2001, each of which is incorporated by reference herein in its entirety.

BACKGROUND OF THE INVENTION

Field of the Invention

This invention relates to the prophylactic and therapeutic use in mammals, particularly man, of dantrolene and its salts, relatives and analogs. Low volume safe for injection formulations of dantrolene provide improved prevention and treatment for currently recognized indications, including malignant hyperthermia, and enable practical use of dantrolene in the field, thus extending its pharmaceutical use to novel applications. The invention further relates to the use of dantrolene in the prophylaxis and treatment of cerebrospinal injury or and cognitive dysfunction secondary to iatrogenically induced states of altered blood flow, including those incurred during surgical procedures involving CPB or related procedures and those which are trauma induced, including pump-head, as well as those incurred during non-normothermic episodes caused iatrogenically or by disease.

DEFINITIONS

"Altered blood flow"—blood flow that exists, and thus has a nonzero flow rate, but is significantly different from normal. For altered blood flow that represents a reduction in pressure, this is considered to be greater than a 10% decrease from baseline systolic pressure, or associated decrease in mean arterial pressure, but less than 95% decrease. Pulsatile changes or temporary elevations in blood pressure are also to be considered altered blood flow.

"Central Nervous System (CNS)"—that portion of the nervous system consisting of the brain and spinal cord (pars centralis systematic nervosa (NA) and systema nervosum centrale (NA alternative)" (Dorland's Medical Dictionary, p. 1652).

"Cerebrospinal System"—that portion of the nervous system comprised of the brain (cerebrum, cerebellum, and brainstem) and spinal cord (white and gray matter) to the level of the conus medularis, but absent the cranial nerves (CN I-XII) as well as the components of the peripheral nervous system.

"Colloidal"—in the current context, a formulation is colloidal if the active compound is present in distinct particles which are primarily micron or submicron in size, in particular less than about 100 microns in average diameter, and in the present context more preferably less than about 2 microns in average diameter.

"Hypoxia"—a state of decreased oxygen supplies available to tissues below normal physiologic levels despite adequate tissue perfusion that can induce states of neuropsychiatric changes and cognitive dysfunction. This may be induced by anemic hypoxia, histotoxic hypoxia, or stagnant hypoxia. Conditions of ventilation/perfusion mismatch as induced by certain pulmonary disease conditions, mechanical or assisted ventilation, or an inadequate concentration of oxygen (insufficient FiO2), may induce a state of hypoxia. Accidental hypothermia, such as that associated with exposure, may also induce hypoxia.

"Low-mannitol" formulation means a formulation of dantrolene (or a salt thereof) that comprises less than 30 milligrams of mannitol per milligram of dantrolene.

"Low-volume formulation" means a formulation of dantrolene (or a salt thereof) that requires less than 100 ml of liquid, and preferably less than 10 ml of liquid, in order to deliver a therapeutic dose of about 300 mg.

"Neuropathy"—a general term denoting functional disturbances and/or pathological changes in the peripheral nervous system." (Dorland's Medical Dictionary, p. 1652).

"Normothermia"—the preferred body temperature at which humans and most mammals exist and thrive, normally a very narrow temperature range (the interthreshold range), being auto-regulated chiefly by the hypothalamus. Hypothermia in humans is largely regarded as being a core body temperature of less than 36 degrees C. In humans, raising the temperature even a fraction of a degree induces vasodilatation and sweating, resulting in hyperthermia. While under the influence of general anesthesia, humans, and most mammals are considered to be poikilothermic; that is, they lose the ability to reliably regulate a state of normothermia and their core body temperatures tend to drift toward the ambient environmental temperature.

"Peripheral Nervous System"—that portion of the nervous system consisting of the nerves and ganglia outside the brain and spinal chord (pars peripherica systematic nervous (NA) and systema nervosum periphericum (NA alternative)." (Dorland's Medical Dictionary, p. 1656).

"Safe for injection". We define "safe for injection" to mean a formulation that can be reliably injected intravenously into appropriate test subjects or model mammals, at relevant clinical doses, with a low incidence of life-threatening complications due to the formulation, where low incidence means less than about 10% of cases, and preferably less than about 1% of cases. In particular, formulation-related toxicities, such as pulmonary emboli (PE) due to supermicron-sized particles or aggregates, pathologically altered arterial pressures, or severe vascular damage, must be limited to low incidence. It is important to point out that in the context of the current patent, the term "safe for injection" does not in any way imply a restriction of a drug formulation to intravenous injection, it merely means that the formulation is sufficiently safe so as to allow intravenous injection. The reason for focusing on the intravenous route with regard to the safety issue is that even when a formulation is administered by another route of injection, such as intramuscular, intra-arterial, subcutaneous, intraperitoneal, intraocular, or by local instillation, the danger of inadvertent routing to a vein cannot be ignored, and often demands that the formulation be safe even if errant administration results in what is essentially an intravenous administration. Because of this, in this patent we use the terms "safe for intravenous injection" and "safe for injection" interchangeably.

"Salt of dantrolene"—a pharmaceutically acceptable salt of dantrolene, in which the counter ion to the dantrolene anion is chosen from the group consisting of sodium (the preferred counter ion), potassium, ammonium, calcium, or magnesium; other possible cations that could be used against dantrolene in the context of this invention include benzyltrimethylammonium, tetramethylammonium, N-methylpyridinium, tetrabutylammonium, 2-(2,3-dihydroxy-1-propylamino)-quinolizinium, Safranine O, quinolizinium, quinolizinium, 2-carbamoyl-1-methylpyridinium, 2,3-dimethyl-1-phenyl-4-trimethyl-ammonium-3-pyrazolin-5-one, dimethylammonium, 1,3-dimethylimidazolium, 2,3-dimethyl-1-phenyl-4-trimethyl-ammonium-3-pyrazolin-5-one, 2-(1-hydroxy-2-methyl)propyltrimethylammonium, and choline.

"Treatment", "Therapeusis"—each of these terms includes both prophylactic (pretreatment) and therapeutic treatment.

DESCRIPTION OF THE PRIOR ART

Altered or impaired cognitive function, neuropsychiatric changes, and motor function are associated with non-specific mechanisms linked to decreased systemic blood pressure, decreased cerebral perfusion and perfusion pressures, and low blood flow states.

Complete interruption of blood supply and embolic phenomena associated with the localized cessation of blood flow, as in the case of stroke, ischemia, and resultant reperfusion injuries are known to initiate a complex cascade of physiologic events, causing peripheral damage, as well defined by Mangat et al. in U.S. Pat. No. 6,462,066. Localized blood flow cessation and subsequent reperfusion in the peripheral vessels of the eye, and associated visual disorders, were of particular focus in the latter patent. The neuropathies that were the subject of the patent by Mangat et al. are all in fact peripheral by definition, according to the standard definition of the term "neuropathy" as recorded by, for example, Dorland's Medical Dictionary (p. 1652).

However, various iatrogenically induced events as well as trauma may alter systemic blood pressure in a much less dramatic fashion, e.g., temporarily decreasing cerebral blood flow, and it is now beginning to be recognized that such altered blood flow, manifested in the central nervous system, can induce neuropsychiatric changes, impair cognitive function, and alter motor function and control. Such alterations may result in either self-limiting or permanent neurologic sequellae. Such conditions are not recognized in the patent of Mangat et al. as being treatable by the methods of that patent, and in fact are not the subject of specific medication-based preventive measures in the current medical practice. Nor are cerebrospinal conditions resulting from such altered blood flow situations recognized as preventable in the US Patent Application Pub. No. 2004/0006124 of Dong, which focuses on neuroretinopathies.

In the case of CNS disturbances, administration of potentially therapeutic agents by injection can be highly problematic, even dangerous, when standard compositions and protocols that apply in treatment of peripheral disturbances are applied in accordance with ordinary skill in that art. In particular, for the treatment of CNS disturbances, large volumes of administration and the presence of excipients that compromise the blood-brain barrier are often contraindicated. Such complications are neither recognized nor addressed by U.S. Pat. No. 6,462,066, further underscoring the limitation of that subject matter to peripheral tissues.

A number of therapeutic agents have been discussed or experimented with in attempts to prevent or reduce cerebrospinal damage resulting from ischemic stroke. These include DP-b99, nimodipine, flunarizine, ebselen, tirilazad, clomethiazole, diazepam, GYKI 52466, NBQX, YM90K, YM872, ZK-200775, SYM 2081, AR-RI5896, aptiganel, dextromethorphan, magnesium, memantine, MK-801, NPS 1506, remacemide, ACEA 1021, GVI50526, eliprodil, ifenprodil, FGF, Anti-ICAM, Hu23F2G, lubeluzole, naloxone, nalmefene, citicoline, Bay x 3072 repinotan, fosphenytoin, 619C89, BMS-204352, cerebrolysin, and piracetam. Most if not all of these attempts have resulted in little if any improvement. See Sandercock et al., Health Technology Assessment, 2002, vol. 6(26), page 27.

U.S. Pat No. 6,187,756 to Lee focuses on treatment of disorders mediated by Amyloid Precursor Protein (APP), such as Alzheimer's disease, in particular on the use of beta-adrenergic receptor antagonists. U.S. Pat. No. 5,506,231 to Lipton deals with disorders mediated by the HIV-1 coat protein gp120. While these patents deal with CNS disorders, they do not teach of treatments, nor especially pre-treatments, for disorders that result immediately—including in humans not previously suffering from factors threatening cerebrospinal health—from altered blood flow such as that associated with cardiopulmonary bypass and other surgical procedures.

Dantrolene is the rescue agent of choice in the treatment of malignant hyperthermia and is therefore widely available in most locations where anesthetics are delivered. First synthesized in 1967, dantrolene was used initially in the treatment of muscle spasms in 1975, and later received FDA approval in 1979 for treating the crisis of MH. More broadly, dantrolene is of value in a range of other conditions requiring a powerful muscle relaxant and treatment against nerve spasticity. As particularly important examples, dantrolene has been of interest and use in the prophylaxis and treatment of other life-threatening conditions such as overdose from recreational drugs such as "ecstasy" (N-methyl-3,4-methylene-dioxyphenylisopropylamine, CAS #42542-10-9), heat stroke, neuroleptic malignant syndrome, and ischemic damage to the peripheral nervous system, and may be of importance in the prevention of sudden infant death syndrome (SIDS).

A derivative of hydantoin-furan, dantrolene sodium is poorly soluble in water. The currently marketed formulation, Dantrium® Intravenous, (Proctor & Gamble, Cinn, Ohio) exists in a lyophilized state, containing 20 mg of dantrolene sodium and 3000 mg of mannitol in a 70 ml sterile vial. A final concentration of 0.33 mg/ml of dantrolene and 50 mg/ml mannitol is achieved upon reconstitution with 60 ml sterile water. As such, this formulation exhibits a number of undesirable properties due in large part to the poor solubility characteristics of dantrolene. These problems have been well described by others and include cumbersome and some times imprecise preparation, significant time and elevated temperatures to prepare a solution suitable for intravenous administration (Grass et al), large volume of solution (600 ml minimum for individual) to deliver an efficacious dose typically ranging from 2.5 to 10.0 mg/kg. See MHAUS, H. Rosenberg, Clinical Anesthesia, 4th Ed. The pH of 9.5 in current formulations is irritating and increases the potential for tissue necrosis secondary to extravasation and endothelial vascular damage (thrombophlebitis). Dissolution of the currently marketed Dantrium® formulation according to the protocol currently practiced in actual MH crises has been shown to be incomplete, strongly indicating that large crystals of dantrolene are being injected intravenously in patients whose cardiovascular state is already under extreme stress. Furthermore, the large loading of mannitol in currently marketed formulations can cause CNS complications.

Deaths have been attributed to the cumbersome preparation of the currently marketed dantrolene formulation, due to the excessive time and effort required for reconstitution, as well as the resultant inaccurate dosing and lack of portability.

Current recommendations by the Malignant Hyperthermia Association of the United States (MHAUS) stipulate that all locations where general anesthetics are administered have 36 vials of dantrolene sodium (720 mg) on hand at all times. In most operative suites, a dedicated MH Cart is equipped with 6 six packs of Dantrium® and liters of sterile water for its reconstitution, as well as 60 cc syringes and needles with which to prepare it, and central line kits, sodium bicarbonate, and other disposables required for administration via central access as opposed to peripheral veins. Reconstitution and injection of several dozen vials of Dantrium® in the face of a fulminant MH crisis is a daunting task, often requiring the assistance of several anesthesia personnel, and these time constraints frequently result in incomplete dissolution of the dantrolene prior to injection and/or treatment delays that can result in harm to the patient.

Others have previously reported their experiences in attempting to improve upon the currently available product. Phospholipid-coated microcrystal formulations (see, viz., U.S. Pat. No. 5,091,188) of dantrolene and dantrolene sodium have been evaluated in normal and MHS swine, but found to be unsafe for injection. See Karan et al., Anesth. Analg. 1996, 52:796. Investigators were challenged in creating uniform particle sizes, ranging in size from 500 nm to 6 microns in size, which resulted in variable treatment results and cardiovascular collapse in some swine believed to be due to either large particles or spontaneous particle agglomeration resulting in pulmonary emboli. Phospholipid-coated dantrolene sodium was found to aggregate, making it unacceptable for injection, and formulations of the free acid form (dantrolene) failed in a significant fraction of cases tested, including when used as a pretreatment prior to exposure to halothane and succinylcholine in pigs (a standard, accepted test for dantrolene effectiveness). Incidences of death and severe complications due to the formulation in these studies was significantly greater than 10% of the animals tested. Furthermore, the phospholipid-coated dantrolene crystal formulation was significantly less potent than the marketed Dantrium® formulation in twitch tension tests on rats, with the reported ED50 being 1.0 mg/kg instead of the 0.6 mg/kg for the marketed formulation, and there is reason to believe that pharmacokinetics may have been significantly retarded as well.

Dantrolene sodium in solution over time precipitates the free acid form, which is unacceptable for an injectable formulation. This probably precludes the possibility of an aqueous formulation of dantrolene sodium with adequate shelf-life. Nevertheless, for a dry formulation, the final administration of the formulation will generally involve reconstitution into an injectable liquid, which is typically, and preferably, water.

Methods have been described in the literature for the preparation of colloidal suspensions of pharmaceutical compounds, including those that are pharmaceutically-acceptable for injection. Usually the crystals are freeze-dried into a powder that can be re-dispersed in water. This approach has mainly been used for orally administered formulations. For injectable formulations, it is crucial that the powder re-disperse as an ultrafine dispersion, with an extremely low incidence of particles or aggregates greater than 1 micron in effective size. In those unusual instances where attempts have been made to prepare dried powder formulations for rapid reconstitution into a safe-for-injection dispersion, some attempts have failed due to the unsuitability of the active drug compound for the methods used. This is particularly true for compounds that have appreciable solubility in water, since most pharmaceutical milling processes are based on aqueous milling.

Dantrolene sodium, the form of dantrolene currently marketed in Dantrium® is currently designed to be reconstituted as an aqueous solution (as opposed to dispersion) for injection, leading to the tacit assumption that its water solubility may be prohibitively high for these standard methods, and likewise to formulation efforts focused on the use of water-insoluble coatings. The latter (in particular the phosphatidylcholine-based coatings investigated by Karan et al.) have proven unsafe for injection, and are in general contraindicated in the case of dantrolene since rapid onset of action is imperative, and because water-insoluble coatings can increase toxicity on injection due to particle size issues.

SUMMARY OF THE INVENTION

It is one object of the present invention to provide dantrolene, or one of its salts, analogs or relatives, in a pharmaceutically acceptable formulation that can deliver the requisite amount of drug in a liquid volume that is greatly reduced from that required by the currently marketed injectable Dantrium® formulation (which requires volumes on the order of 500 ml to 1800 ml for a human application), and which therefore minimizes or circumvents the complications and dangers associated with reconstituting large liquid volumes of multiple vials of lyophilized agent for administration, including but not limited to the treatment of some of the conditions of focus in this patent.

This substantial reduction in volume and associated problems is not foreseen in the Mangat et al. patent, but should be considered of high importance in view of, for example, the added complications imposed when 500-1,800 ml of aqueous solution must be reconstituted and administered in a procedure whose success is dependent on rapid intervention, critical control of an extracorporeal circuit, and/or where intravascular volume expansion may be relatively or absolutely contraindicated. With certain embodiments of the current invention, a dantrolene dose of up to 500 mg can be delivered in a liquid volume less than or equal to about 150 ml; a 300 mg dose can be delivered in a volume of less than or equal to about 100 ml, more preferably less than or equal to about 30 ml, and most preferably less than or equal to about 5 ml. The latter volume is sufficiently small that the entire formulation could be loaded into an auto injector in accordance with standard volumes of such devices, thus providing for portability as required by field and ambulance applications.

It is a further object of this invention to provide a low-volume formulation of dantrolene or one of its salts that is either a solution, or contains particles that are sufficiently small to permit safe administration via all conceivable routes, certainly including but not limited to intravenous, intramuscular, intrathecal, and extracorporeal fluids and/or circuits, in particular such that over 95% of the particles are less than 0.8 microns, or preferably less than 0.45 microns. Such sizes are important not only for safety against pulmonary emboli on injection, but also against microbial infections since they can allow for filtration, e.g., using an in-line filter, at sizes that exclude at least some of the most important microbes.

It is a further an object of this invention to provide formulations of dantrolene that are rapidly and reliably reconstituted in emergency clinical situations, as well as in non-emergency and prophylactic circumstances. In particular, the formulations will be such that a full therapeutic dose of 300 mg can be reconstituted in a clinical situation in under 1 minute by a single clinician.

It is a further object of this invention to provide a dry powder formulation of sodium dantrolene, or of another salt of dantrolene, that shows minimal appearance of the free acid dantrolene during storage.

It is a further object of this invention to provide a pharmaceutically acceptable low-volume dantrolene sodium formulation that contains low mannitol content, less than about 30 mg of mannitol per milligram of dantrolene, thus permitting safer use in indications where neurological complications may occur.

It is an object of this invention to provide a method for treating malignant hyperthermia and other and related conditions as identified in this application, including but not limited to MDMA overdose and heat stroke, by the use of a safe-for-injection, low-volume colloidal suspensions of dantrolene or one of its salts.

It is a further object of this invention to provide safe, low-volume and low-mannitol colloidal suspensions of dantrolene that overcome these problems, improving treatment of MH and related conditions in the operating room, and making efficacious treatment more widely available in other settings, and other etiologies. Thus, it is an object of the invention to provide dantrolene, or one of its salts, analogs or relatives, in a pharmaceutically acceptable formulation that can deliver the requisite amount of drug in a liquid volume that is greatly reduced from that required by the currently marketed injectable Dantrium® formulation (which requires volumes on the order of 500 ml to 1800 ml for a human application), and which therefore minimizes or circumvents the complications and dangers associated with reconstituting large liquid volumes of multiple vials of lyophilized agent for administration, including but not limited to the treatment of some of the conditions of focus in this patent.

Another aspect of this invention centers around a class of new indications for the use of the dantrolene. In particular, it is an object of this invention to provide a method by which to prevent, reduce or reverse the negative cerebrospinal and cognitive injuries, described herein, which can be associated with altered, and especially decreased, blood pressures; altered, and especially decreased, blood flow; altered, and especially decreased cerebral perfusion; altered, and especially diminished pulsatile flow, as well as increased intracranial pressures which inherently alter, and especially impair cerebral perfusion and subsequent oxygenation of cerebral tissues; and non-normothermic states especially those which are sustained for more than about four hours. The phenomena of altered cognitive abilities and function as well as neuropsychiatric changes with or without impaired motor function is commonly referred to as "pumphead" among anesthesiologists, cardiothoracic surgeons, and certain other medical personnel. In particular, in this patent, it is envisioned that the prophylactic administration of dantrolene, or one of its salts, analogs or relatives, may prevent or limit the effects of these neurological complications via a unique and synergistic combination of a number of intracellular and/or metabolic mechanisms, and via stabilization of intracellular calcium. It is further expected that dantrolene will be a suitable treatment agent capable of minimizing neurological complications when provided in a manner timely to the insult, not only in humans but potentially in veterinary settings as well.

DETAILED DESCRIPTION OF THE INVENTION

The current invention focuses on new formulations, and indications, of dantrolene and dantrolene salts that are safe for injection and require only small liquid volumes for administration, less than about 100 ml and preferably less than about 10 ml for the administration of a typical therapeutic dose of about 300 mg. It is largely anticipated that this invention will allow for unit dosing in convenient, single-dose lyophilized or predispersed material. This will allow for accurate administration either corporally or extracorporally with a minimum of manipulation. The large-volume workup of the current Dantrium® formulation greatly interferes with the practicality of field use of dantrolene, such as in military or ambulance applications, whereas the low-volume formulations presented herein could be especially useful in such field applications. Similarly, the invention could have value in public health situations requiring administration away from the clinic, such as in the event of a disease epidemic, or wartime or terrorist-related injuries, etc.

These formulations are colloidal suspensions of dantrolene or its salts in a pharmaceutically acceptable liquid, preferably chosen from the group consisting of water, glycerol, propylene glycol, dimethylacetamide, ethanol, polyethylene glycol (e.g., PEG 300, PEG 400, PEG 3350), triethyl citrate, triacetin, monothioglycerol, or mixtures thereof, more preferably water or a water-miscible solvent, and most preferably water. The invention also discloses dry powder formulations of dantrolene or one of its salts that can be rapidly (less than one minute) reconstituted by adding a pharmaceutically acceptable liquid, preferably sterile water for injection, and mechanically agitating, preferably by hand shaking.

Another significant advantage of the invention as described herein, in addition to providing safe-for-injection, rapidly reconstitutable and administrable dantrolene formulations, is the reduction or omission of mannitol from the currently marketed formulation. Mannitol functions as an intravascular osmotic gradient inducer drawing extravascular fluids to the intravascular space. This may prove beneficial in treating certain types of edemas. However, in many surgical situations involving neurological complications, mannitol is widely recognized to be contraindicated. In such a state, the mannitol leaves the intravascular space, becoming extravascular and collecting in the region of the disrupted blood brain barrier. Extravascularly, it creates a similar osmotic gradient, but here it causes free fluid accumulation in the cerebral tissue, increasing cerebral edema, increasing intracranial pressures while decreasing cerebral blood flow via alteration of cerebral perfusion pressures.

Furthermore, an additional advantage of the precisely controlled nanoparticle size of our colloidal suspension is that distribution of dantrolene to poorly perfused skeletal muscle in a state of active tetany can be maximized. It has been theorized that in some instances of failed treatment of MH, that the crisis had evolved to a point where tetanic contraction of muscle severely interrupted the delivery of larger sized particles or crystals of dantrolene, rendering it unavailable to the binding site while appropriate concentration were achieved elsewhere in the intravascular compartment.

It is anticipated that a wide range of doses of this low-volume, low-mannitol dantrolene sodium formulation will obtain the intended effect of alleviating an MH crisis or related event. A lower volume formulation as provided herein, will allow for easier and more accurate administration in a more rapid manner than prior art formulations. At this time, it is expected that doses ranging from 0.1 to 10.0 mg/kg will prove efficacious, depending upon the age, pre-existing state of health, and possible extent of neurologic injury depending upon the type and extent of the insult. The preferred range is about 0.5 to about 4 mg/kg.

In addition, another aspect of the invention is the discovery of new indications for dantrolene, for which existing dantrolene formulations as well as low-volume formulations as disclosed herein provide for a new method of treatment and prophylaxis. The inventors have recognized that dantrolene provides a surprising and synergistic combination of biochemical and pharmacologic mechanisms that make it of unique applicability in the prevention and treatment of certain cerebrospinal, and especially cognitive, injuries which prior to this invention were poorly understood and even more poorly treated. Attention to such injuries, particularly when their symptomology is "silent", and sometimes delayed, following in the aftermath of certain surgical procedures, has in previous medical practice taken a back seat to the primary surgical indication. Of these injuries, cognitive loss sometimes referred to as "pumphead" is a representative example.

Materials and Methods for Making Colloidal Dantrolene of the Current Invention

Colloidal dispersions of submicron crystals of dantrolene or one of its salts, that are safe for injection, can be prepared according to known methods of particle size reduction in pharmaceutical patents, literature, and practice. High-pressure homogenization and wet-milling are two general methods. For a representative discussion of milling techniques in pharmaceutical settings see, for example, U.S. Pat. No. 5,858, 410 (which is herein incorporated by reference). An important aspect of this invention is the realization that the water solubility of sodium dantrolene is low enough that these methods can in fact be applied. This is of fundamental importance because not only is the sodium salt of dantrolene the salt that is in the currently marketed formulation of dantrolene, with a long history of safe use, but also our work indicates that the dissolution of the free acid, for example, is significantly slower and more problematic than that of dantrolene sodium, which is of importance in the safety of an injectable product. The Examples below illustrate these two general methods of production. Other methods include dry-milling, chemical precipitation, spray-drying (e.g., from aqueous solution, generally containing a stabilizer as discussed below), sonication, solvent-removal from template emulsions, evaporative precipitation into aqueous solutions, and supercritical fluid-based methods such as Precipitation with Compressed Antisolvent.

Alternatively, more complicated microparticles can be produced which contain dantrolene or one of its salts dispersed or dissolved within the core of the microparticle. For example, submicron dantrolene crystals can be embedded within lyotropic liquid crystals, which in turn can be coated, as per U.S. Pat. No. 6,482,517 (which is herein incorporated by reference), or within particles or microfibers of one or more biocompatible polymers, such as PLGA, collagen, carboxymethylcellulose or other cellulosic polymer, albumin, casein, PVP, etc.

The size of the particles of dantrolene or dantrolene salt or relative in the formulation as per this invention is very important, particularly in determining whether it is safe for injection. It should also be noted that in the case of a lyophilized, dry powder formulation as per this invention, particles of drug (dantrolene or one of its salts, relatives, or analogs) which are present in the dry formulation in submicron particle sizes may nevertheless be embedded in solids that are much larger, even as large as millimeters in size, provided that these latter solids are readily dissolved in the carrier liquid (usually water) that is added during reconstitution. For example, submicron crystals of dantrolene sodium could be embedded in a solid or amorphous saccharide, such as lactose or trehalose, in which case the size of the overall solid particles could be much larger than submicron; addition of water would quickly dissolve the saccharide in this case, and leave behind submicron crystals of drug, making the reconstituted formulation safe for intravenous injection.

In a dry powder formulation, in addition to sufficiently small (generally less than about 2 microns, and preferably less than about 0.8 microns and more preferably less than about 0.45 microns) dantrolene particle size, another feature that is important, and which also distinguishes dried formulations of this invention from prior art dried forms of dantrolene, is that the surface chemistry of the formulation ensures dispersibility, upon reconstitution. In particular, the incorporation of stabilizers and in some cases dispersants (or, components such as PVP which can serve as both stabilizer and dispersant) in the dried formulation as discussed herein is done so as to ensure dispersibility upon addition of liquid, usually sterile water for injection. In contrast, addition of 3 to 150 milliliters of water to a simple powder of dantrolene sodium (as received from Sigma-Aldrich Chemical Company, for example), or to the Dantrium formulation, and subsequent shaking by hand at room temperature would not yield a safe for injection dispersion, since the particle size would be too large, as reported by Mitchell and Leighton in Gen. Anesth., 2003, vol. 50(2), p. 127. Furthermore, the absence of stabilizers in these cases would yield particles that would very quickly begin to settle into the bottom of a reconstitution vial, or syringe.

The colloidal suspensions of dantrolene or its salts in the current invention comprise crystals of dantrolene, a dantrolene salt, or a related muscle relaxant compound suspended or dispersed in a pharmaceutically acceptable liquid, preferably chosen from the group consisting of water, glycerol, propylene glycol, dimethylacetamide, ethanol, polyethylene glycol (e.g., PEG 300, PEG 400, PEG 3350), triethyl citrate, triacetin, monothioglycerol, or mixtures thereof, more preferably water or a water-miscible solvent, and most preferably water. Broadly, a stabilizer is usually required in order to achieve a stable, fine dispersion of crystals (or amorphous drug substance), and the stabilizer if required is preferably chosen in accordance with the following. Stabilizers of use include select proteins, polymers, and surfactants. The proteins of potential use as stabilizers include albumin, casein, and salts of casein. Polymers include polyvinylpyrrolidone (PVP), acacia (gum arabic), carmellose sodium, dextran, collagen, gelatin, gelatin hydrosylate, sodium starch glycolate, inulin, and xanthan. Suitable surfactants or block copolymer components (or mixtures thereof) may include:

a. cationic surfactant
b. anionic surfactant
c. semipolar surfactant
d. zwitterionic surfactant
   i. in particular, a phospholipid
   ii. a lipid mixture containing phospholipids, designed to match the physico-chemical characteristics of a biomembrane
e. monoglyceride
f. PEGylated surfactant
g. one of the above but with aromatic ring
h. block copolymer
   i. with both blocks hydrophobic, but mutually immiscible
   ii. with both blocks hydrophilic, but mutually immiscible,
   iii. with one block hydrophilic and the other hydrophobic, i.e., amphiphilic)
i. a mixture of two or more of the above.

Suitable lipids include phospholipids (such as phosphatidylcholine, phosphatidylserine, phosphatidylethanolamine, or sphingomyelin), or glycolipids (such as MGDG, diacylglucopyranosyl glycerols, and Lipid A). Other suitable lipids are phospholipids (including phosphatidylcholines, phosphatidylinositols, phosphatidylglycerols, phosphatidic acids, phosphatidylserines, phosphatidylethanolamines, etc.), sphingolipids (including sphingomyelins), glycolipids (such as galactolipids such as MGDG and DGDG, diacylglucopyranosyl glycerols, and Lipid A), salts of cholic acids and related acids such as deoxycholic acid, glycocholic acid, taurocholic acid, etc., gentiobiosyls, isoprenoids, ceramides, plasmologens, cerebrosides (including sulphatides), gangliosides, cyclopentatriol lipids, dimethylaminopropane lipids, and lysolecithins and other lysolipids which are derived from the above by removal of one acyl chain.

Other suitable types of surfactants include anionic, cationic, zwittenionic, semipolar, PEGylated, amine oxide and aminolipids. Preferred surfactants are:

anionic—sodium oleate, sodium dodecyl sulfate, sodium diethylhexyl sulfosuccinate, sodium dimethylhexyl sulfosuccinate, sodium di-2-ethylacetate, sodium 2-ethylhexyl sulfate, sodium undecane-3-sulfate, sodium ethylphenylundecanoate, carboxylate soaps of the form ICn, where the chain length n is between 8 and 20 and I is a monovalent counterion such as lithium, sodium, potassium, rubidium, etc.;

cationic—dimethylammonium and trimethylammonium surfactants of chain length from 8 to 20 and with chloride, bromide or sulfate counterion, myristyl-gammapicolinium chloride and relatives with alkyl chain lengths from 8 to 18, benzalkonium benzoate, double-tailed quaternary ammonium surfactants with chain lengths between 8 and 18 carbons and bromide, chloride or sulfate counter ions;

nonionic PEGylated surfactants of the form CnEm where the alkane chain length n is from 6 to 20 carbons and the average number of ethylene oxide groups m is from 2 to 80, ethoxylated cholesterol;

zwitterionics and semipolars—N,N,N-trimethylaminodecanoimide, amine oxide surfactants with alkyl chain length from 8 to 18 carbons; dodecyldimethylammoniopropane-1-sulfate, dodecyldimethylammoniobutyrate, dodecyltrimethylene di(ammonium chloride); decylmethylsulfonediimine; dimethyleicosylammoniohexanoate and relatives of these zwitterionics and semipolars with alkyl chain lengths from 8 to 20.

Preferred surfactants, including preservatives which are used as surfactants, which are FDA-approved as injectables include benzalkonium chloride, sodium deoxycholate, myristyl-gamma-picolinium chloride, Poloxamer 188 (Pluronic F-68). Pluronic F-127, polyoxyl castor oil and related PEGylated castor oil derivatives such as Cremaphore EL, Arlatone G, sorbitan monopalmitate, Pluronic 123, and sodium 2-ethylhexanoic acid. Other low-toxicity surfactants and lipids, which are of at least relatively low solubility in water, that are preferred for the present invention for products intended for a number of routes of administration, include: acetylated monoglycerides, aluminum monostearate, ascorbyl palmitate free acid and divalent salts, calcium stearoyl lactylate, ceteth-2, choleth, deoxycholic acid and divalent salts, dimethyldioctadecylammonium bentonite, docusate calcium, glyceryl stearate, stearamidoethyl diethylamine, ammoniated glycyrrhizin, lanolin nonionic derivatives, lauric myristic diethanolamide, magnesium stearate, methyl gluceth-120 dioleate, monoglyceride citrate, octoxynol-1, oleth-2, oleth-5, peg vegetable oil, peglicol-5-oleate, pegoxol 7 stearate, poloxamer 331, polyglyceryl-10 tetralinoleate, polyoxyethylene fatty acid esters, polyoxyl castor oil, polyoxyl distearate, polyoxyl glyceryl stearate, polyoxyl lanolin, polyoxyl-8 stearate, polyoxyl 150 distearate, polyoxyl 2 stearate, polyoxyl 35 castor oil, polyoxyl 8 stearate, polyoxyl60 castor oil, polyoxyl 75 lanolin, polysorbate 85, sodium stearoyl lactylate, sorbitan sesquioleate, sorbitan trioleate, stear-o-wet c, stear-o-wet m, stearalkonium chloride, stearamidoethyl diethylamine (vaginal), steareth-2, steareth-10, stearic acid, stearyl citrate, sodium stearyl fumarate or divalent salt, trideceth 10, trilaneth-4 phosphate, Detane PB, JBR-99 rhamnolipid (from Jeneil Biosurfactant), glycocholic acid and its salts, taurochenodeoxycholic acid (particularly combined with vitamin E), tocopheryl dimethylaminoacetate hydrochloride, tocopheryl phosphonate, tocopheryl peg 1000 succinate, cytofectin gs, 1,2-dioleoyl-sn-glycero-3-trimethylammonium-propane, cholesterol linked to lysinamide or ornithinamide, dimethyldioctadecyl ammonium bromide, 1,2-dioleoyl-sn-3-ethylphosphocholine and other double-chained lipids with a cationic charge carried by a phosphorus or arsenic atom, trimethyl aminoethane carbamoyl cholesterol iodide, lipoic acid, O,O'-ditetradecanoyl-N-(alpha-trimethyl ammonioacetyl) diethanolamine chloride (DC-6-14), N-[(1-(2,3-dioleyloxy)propyl)]-N—N—N-trimethylammonium chloride, N-methyl-4-(dioleyl)methylpyridinium chloride (saint-2), lipidic glycosides with amino alkyl pendent groups, 1,2-dimyristyloxypropyl-3-dimethylhydroxyethyl ammonium bromide, bis[2-(11-phenoxyundecanoate)ethyl]-dimethylammonium bromide, N-hexadecyl-N-10-[O-(4-acetoxy)-phenylundecanoate]ethyl-dimethylammonium bromide, bis[2-(11-butyloxyundecanoate)ethyl] dimethylammonium bromide, 3-beta-[N—(N',N'-dimethylaminoethane)-carbamoyl] cholesterol, vaxfectin, cardiolipin, dodecyl-N,N-dimethylglycine, and lung surfactant (Exosurf, Survanta). Suitable block copolymers are those composed of two or more mutually immiscible blocks from the following classes of polymers: polydienes, polyallenes, polyacrylics and polymethacrylics (including polyacrylic acids, polymethacrylic acids, polyacrylates, polymethacrylates, polydisubstituted esters, polyacrylamides, polymethacrylamides, etc.), polyvinyl ethers, polyvinyl alcohols, polyacetals, polyvinyl ketones, polyvinylhalides, polyvinyl nitriles, polyvinyl esters, polystyrenes, polyphenylenes, polyoxides, polycarbonates, polyesters, polyanhydrides, polyurethanes, polysulfonates, polysiloxane, polysulfides, polysulfones, polyamides, polyhydrazides, polyureas, polycarbodiimides, polyphosphazenes, polysilanes, polysilazanes, polybenzoxazoles, polyoxadiazoles, polyoxadiazoiidines, polythiazoles, polybenzothiazoles, polypyromellitimides, polyquinoxalines, polybenzimidazoles, polypiperazines, cellulose derivatives, alginic acid and its salts, chitin, chitosan, glycogen, heparin, pectin, polyphosphorus nitrile chloride, polytri-n-butyl tin fluoride, polyphosphoryldimethylamide, poly.-2,5-selenienylene, poly-4-n-butylpyridinium bromide, poly-2-N-methylpyridinium iodide, polyallylammonium chloride, and polysodium-sulfonate-trimethylene oxyethylene. Preferred polymer blocks are polyethylene oxide, polypropylene oxide, polybutadiene, polyisoprene, polychlorobutadiene, polyacetylene, polyacrylic acid and its salts, polymethacrylic acid and its salts, polyitaconic acid and its salts, polymethylacrylate, polyethylacrylate, polybutylacrylate, polymethylmethacrylate, polypropylmethacrylate, poly-N-vinyl carbazole, polyacrylamide, polyisopropylacrylamide, polymethacrylamide, polyacrylonitrile, polyvinyl acetate, polyvinyl caprylate, polystyrene, poly-alpha-methylstyrene, polystyrene sulfonic acid and its salts, polybromostyrene, polybutyleneoxide, polyacrolein, polydimethylsiloxane, polyvinyl pyridine, polyvinyl pyrrolidone, polyoxy-tetramethylene, polydimethylfulvene, polymethylphenylsiloxane, polycyclopentadienylene vinylene, polyalkylthiophene, polyalkyl-p-phenylene, polyethylene-alt-propylene, polynorbomene, poly-5-((trimethylsiloxy)methyl)norbomene, polythiophenylene, heparin, pectin, chitin, chitosan, and alginic acid and its salts. Especially preferred block copolymers are polystyrene-b-butadiene, polystyrene-b-isoprene, polystyrene-b-styrenesulfonic acid, polyethyleneoxide-b-propyleneoxide, polystyrene-b-dimethylsiloxane, polyethyleneoxide-b-styrene, polynorborene-b-5-((trimethylsiloxy)methyl)norbornene, polyacetylene-b-5-((trimethylsiloxy)methyl)norbornene, polyacetylene-b-norbornene, polyethyleneoxide-b-norbornene, polybutyleneoxide-b-ethyleneoxide, polyethyleneoxide-b-siloxane, and the triblock copolymer polyisoprene-b-styrene-b-2-vinylpyridine.

As discussed above, stabilizers that have significant water solubility, preferably greater than about 5 mg/ml, are inherently safer than those which are less soluble than 5 mg/ml.

Methods for removing water from aqueous-based dispersions in order to create reconstitutable dry powders are well known to those skilled in the art of parenteral products. Lyophilization, or freeze-drying, of an aqueous dispersion according to standard pharmaceutical procedures can be applied to colloidal dispersions of dantrolene or one of its salts, preferably dantrolene sodium, so as to produce dry powders that can be reconstituted by the addition of sterile water for injection and shaking or vortexing. See for example U.S. Pat. No. 5,858,410. The use of stabilizers that are solid at room temperature, as opposed to liquid, provides for a better freeze-dried product in general, and strongly hygroscopic stabilizers are also less preferred. Preferred stabilizers for the colloidal dispersions of the current invention thus include sodium deoxycholate, sodium dodecyl sulfate, PVP, benzalkonium chloride, sodium docusate, hydrolyzed gelatin, and the "F" Pluronics such as F-68 and F-127. Albumin is to be avoided, particularly in large amounts relative to the dantrolene, since albumin binds to dantrolene and this can interfere with the normal activity and pharmacokinetics of the drug. It should be noted that, as discussed elsewhere herein, highly insoluble stabilizers are less preferred since they can interfere with the pharmacokinetics of dantrolene—unless, as illustrated in Example 4, they are present (in the final, possibly reconstituted formulation) in the form of a nanoporous, reversed lyotropic liquid crystalline phase, such as a cubic phase, which can actually promote absorption. Dispersing agents can also be added, such as saccharides like lactose, trehalose, sorbitol, sucrose, dextrose, mannitol, and such, with lactose, sorbitol, and mannitol especially preferred. Disintegrants, and particularly superdisintegrants, can be used to improve speed and efficiency of reconstitution, and such compounds include PVP and carboxymethylcellulose, both of which are safe for injection when used in sufficiently low amounts.

The forms of dantrolene that can be used in the current invention include dantrolene free acid and a range of pharmaceutically acceptable salts of dantrolene, in which the counter ion to the dantrolene anion is chosen from the group consisting of sodium (the preferred counter ion), potassium, ammonium, calcium, or magnesium; other possible cations that could be used against dantrolene in the context of this invention include benzyltrimethylammonium, tetramethylammonium, N-methylpyridinium, tetrabutylammonium, 2-(2,3-dihydroxy-1-propylamino)-quinolizinium, Safranine O, quinolizinium, quinolizinium, 2-carbamoyl-1-methylpyridinium, 2,3-dimethyl-1-phenyl-4-trimethyl-ammonium-3-pyrazolin-5-one, dimethylammonium, 1,3-dimethylimidazolium, 2,3-dimethyl-1-phenyl-4-trimethyl-ammonium-3-pyrazolin-5-one, 2-(1-hydroxy-2-methyl)propyltrimethylammonium, and choline. Dantrolene free acid can also be used, though it has been found in the course of this work that dissolution of formulations of the free acid are slower and less reliable than in the case of a salt such as the sodium salt. The preferred salt of dantrolene is dantrolene sodium, the currently marketed salt.

The safety and greater portability and more appropriate package size made possible by the current invention will facilitate the broader availability of dantrolene to every surgical suite, emergency room, as well as other specialty or surgical settings, as well as non-surgical and non traditional settings wherever the need may arise, for treatment of MH of any etiology, and for treatment of other indications. Such indications that may be treatable by the colloidal dantrolene formulations of this invention include, but are not limited to, various types of ischemia, heat stroke, overdose or reaction to recreational drugs such as "ecstasy", neuroleptic malignant syndrome (NMS), central core disease (CCD), Duchenne Muscular Dystrophy (DMD), King-Denborough Syndrome, Myoadenylate Deaminase Deficiency (MDD), Schwartz-Jampel syndrome, the Fukuyama type of congenital muscular dystrophy, fibromyalgia, Becker muscular dystrophy, periodic paralysis, myotonia congenita, sarcoplasmic reticulum adenosine triphosphatase deficiency syndrome, Burkett's lymphoma, Sudden Infant Death Syndrome (SIDS), osteogenesis imperfecta, glycogen storage pathologies, mitochondrial myopathies, and alterations in the endoplasmic reticulum associated with Alzheimer's disease, as well as toxic reactions to strychnine, phencyclidine, hemlock, amphetamines, MAO inhibitors, theophylline, LSD and other psychedelic drugs, and cocaine. In general the invention is of potential benefit in the treatment of seizures and muscle contraction-related hyperthermia, in conjunction with antipyretic treatment, as a muscle relaxant, and as a neuroprotective agent in the face of elevated cerebrospinal temperatures. The invention could also be of use in prophylactic treatment of MH during pregnancy. Broadly speaking, the invention can be applied in any condition where the low volume of administration is a significant advantage, including but not limited to increasing portability, ease of use, reliability in dosing, timeliness of dosing, absence of larger undissolved solid material, and improved safety in the face of neurological complications.

The colloidal dantrolene of this invention requires significantly less time for preparation and administration. At this time, we envision colloidal dantrolene will be made available as 3%-8% (30-80 mg/ml) in 5 ml or 10 ml vials either as a stable suspension ready for injection or as a powder to be reconstituted in 10 ml or less of sterile water into a suspension ready for injection. It is anticipated that a full therapeutic dose could be delivered in less than one minute as a bolus injection, easily attaining the 1 mg/kg/min, if not significantly exceeding, recommended rate of administration. A reconstitutable powder would be reconstituted by combining with sterile water for injection and shaken or vortexed; filtration prior to injection may be desirable. Reconstitutable powders of the invention can be reconstituted by a single clinician in less than one minute to a safe-for-injection dispersion.

The colloidal dantrolene of this invention may be formulated at a more physiologic pH, likely reducing the risk of tissue damage and of thrombophlebitis as associated with the extravasation of the current Dantrium® product at pH 9.5. This feature, coupled with the small bolus volume of the colloidal product needed to be administered, will allow injection via peripheral veins through small-bore cannulae (24 gauge), rather than the via central venous access as is frequently recommended.

Dantrolene is widely known to be a muscle relaxant. Therefore, protective measures may have to be undertaken, such as planning for endotracheal intubation and mechanical ventilation. While this technique is commonly practiced during general anesthesia for surgical intervention and to facilitate hyperventilation in the management of the trauma patient, there may be instances where it is impractical or contraindicated to administer dantrolene given this concern. In the instance of known adverse reaction by an individual to dantrolene, its use is contraindicated.

It is within the scope of this invention to provide a safe-for-injection dispersion of dantrolene or one of its salts that is, or can be, pre-loaded into an autoinjector, particularly for field use. A particularly important application of such a formulation/device could be in military or terrorist arenas, where for example the use of chemical or biological warfare agents may be a threat.

Other agents in place of, or in combination with, dantrolene and its salts.

In place of, or in addition to, dantrolene salts, other agents may provide similar protection which may be useful as alternative colloidal formulations, or in conjunction with the colloidal dantrolene preparations described herein. This is particularly true in cases where the agent has similar pharmacologic action as dantrolene sodium, and especially if it is known to provide relief from MH. Thus, a pharmacologically active relative of dantrolene, such as a compound containing a hydantoin group and/or a nitrophenyl or nitrofuranyl group, which affects the ryanidine receptor and through it intracellular calcium release, would be expected to be active within the present invention, particularly if it diminishes the symptoms of MH. As an instructive example, while certain analogues such as azumolene are pharmacologically related to dantrolene and may be of use in the present invention, dantrolene would be preferred over azumolene because the latter has shown limited benefit in the treatment of Malignant Hyperthermia (MH); in contrast, dantrolene sodium is the most efficacious rescue agent known for MH. It is also anticipated that new dantrolene analogs and chemical relatives will become available, and to the extent that such a new agent has similar pharmacologic actions, and especially to the extent that it relieves the symptoms of MH, it is to be expected that the same agent can be used in the context of the present invention.

While dantrolene and its salts are the preferred agents, certain other agents or classes of compounds, especially those agents known to regulate calcium intracellularly, could be of potential benefit in situations or conditions where the use of dantrolene sodium is contraindicated. Calcium channel blockers as a class of drugs is one example of such a substitution. While the effects of such drugs on calcium could be similar to those of dantrolene, it must be recognized that dantrolene has other pharmacologic effects that may be important in the treatments of focus herein and may not be accomplished by such a substitute.

EXAMPLES

Example 1

Dantrolene sodium (synthesized by CarboMer, Inc.), in the amount of 2.40 grams, was added to 27.60 gm of pH 10 buffer, into which had previously been dissolved 0.24 gm of polyvinylpyrrolidone (PVP). This mixture was then loaded into a Model 110L Microfluidizer (Microfluidics Corp., Bedford, Mass.), powered by a Kaeser air compressor. At a pump pressure of 15,000 psi, this was microfluidized for four cycles of 1.5 minutes each.

At the end of this time, examination through a phase contrast optical microscope with a 40× objective, and the particle size was seen to be submicron for a high fraction of the drug crystals. A particle size distribution was then obtained using a Beckman Coulter N4Plus light scattering particle sizer. The mean particle size was found to be 407 nm, with a standard deviation of 21 nm, and 0.0% dust reported; together these indicate an extremely well controlled particle size, and in a size range acceptable for intravenous injection. Zeta potential on the particles was then measured with a Beckman Coulter DELSA 440SX instrument, and indicated an average −54 mV potential and over 90% of the population lying between −80 and −25 mV. Such a strong zeta potential is sufficient to yield long-term dispersion stability via ionic stabilization.

For a dantrolene formulation made according to this protocol, a 240 mg dose of dantrolene sodium could be delivered in a volume of approximately 3 ml.

Example 2

Working in a nitrogen-filled glove box, dantrolene sodium, in the amount of 0.267 grams, was added to a 15 ml tube and then covered with 1.046 gm N,N-dimethylacetamide and 3.164 gm glycerol which had been heat-sterilized. The dantrolene was dissolved in this mixture by a combination of stirring, vortexing and sonicating. Polyethylene glycol 200, in the amount 4.495 gm, and 1N NaOH (0.173 gm) were then added. This mixture, in which the sodium dantrolene was in true solution (e.g. dissolved), was then loaded into 1 ml sterile syringes for injection, and used successfully in live animal tests.

For a dantrolene formulation made according to this protocol, a 240 mg dose of dantrolene sodium could be delivered in a volume of only about 7 ml. Dimethylacetamide is currently used in one injectable product, and animal tests conducted to date suggest that this formulation is safe for injection as defined herein.

Example 3

A colloidal dispersion of dantrolene sodium at 5 mg/ml was prepared by first overlaying 0.101 gm of dantrolene sodium with 20 ml of an aqueous solution of benzalkonium chloride, made by mixing 0.319 gm of benzalkonium chloride in 100 ml of distilled water; the dantrolene sodium is therefore at a level that greatly exceeds the solubility in water (less than 0.4 mg/ml), and nearly all is dispersed as opposed to dissolved. The mixture was then homogenized with a Polytron homogenizer at high speed for 3 minutes, to yield submicron particles. Zeta potential measurements using a Beckmann-Coulter Doppler Electrophoretic Laser Scattering Analyzer (DELSA) showed a zeta potential of +28 mV. Clearly this charge is due to the adsorption of a stabilizing layer of benzalkonium chloride, since the dantrolene sodium would, of course, yield an anionic charge. Benzalkonium chloride is FDA approved in safe-for-injection products.

Example 4

In this Example, a phospholipid-based lyotropic liquid crystal was used as a stabilizing layer on dispersed crystals of dantrolene sodium, again at the high concentration of 50 mg/ml. This was prepared by first preparing a "cubic phase" lyotropic liquid crystal, by mixing 1.595 gm of high-PC soybean phospholipid (Epikuron 200, from Lucas-Meyer, Inc.), 1.121 gm of alpha-tocopherol, and 0.788 gm of distilled water. An amount 0.349 gm of dantrolene sodium was mashed into the liquid crystal. To 0.999 gm of this mixture was added 20 ml of the solution of benzalkonium chloride described in Example 3, and the mixture was then homogenized with a Polytron homogenizer at high speed for 3 minutes, yielding submicron particles. Zeta potential measurements using a Beckmann-Coulter Doppler Electrophoretic Laser Scattering Analyzer (DELSA) in this case showed a zeta potential of +72 mV. There was no evidence of a peak at +28 mV, as in the previous Example, thus indicating that the dantrolene crystals were coated with phospholipid-rich material, which in turn had an outer surface rich in benzalkonium chloride.

Example 5

We tested two novel low volume dantrolene formulations as rescue agents in porcine malignant hyperthermia. Each formulation was a low volume colloidal suspension that dissolves readily upon injection into the blood stream. Formulations of both dantrolene sodium and dantrolene free acid were evaluated as potential less cumbersome alternative treatment articles to Dantrium® IV that can be made immediately available for single bolus dose injection in volumes less than 10 ml for an adult.

The primary goal of this study was to evaluate the efficacy of low volume colloidal suspension dantrolene in the treatment of the crisis of malignant hyperthermia in malignant hyperthermia susceptible swine. We hypothesized that both the sodium and free acid micronized dantrolene formulations would reverse the crisis of MH following bolus intravenous injection of a weight based calculated treatment dose of 2.5 mg/kg.

This study, as well as both preliminary studies, were approved and performed in accordance to the BAS Evansville Institutional Animal Care and Use Committee. Each study was performed as a randomized, open label comparison study performed at a single study center by the same investigators.

In the first preliminary study, two dantrolene sodium and free acid formulations were evaluated for both safety and efficacy in 12 Sprague Dawley rats. Prior to dosing, body weights were obtained and each rat received a single bolus dose injection of their respective test article via the lateral tail vein. All animals were observed immediately post dosing and continuously up through 30 minutes and again at approximately 1, 2, 3, 4, 7, and 24 hours, prior to necropsy.

Example 6

In the second preliminary study, ten non-MHS domestic swine (Yorkshire crossbreed) were used to determine the relative efficacious dose of single formulations of dantrolene sodium and free acid capable of creating muscle relaxation. The methods as originally described by Nelson and Flewellen, were followed, absent a sophisticated muscle-tension force measuring device. All swine were housed in accordance with AALAC principles, acclimated at least 5 days prior to study in individual runs, fed twice daily with water ad libitum, in an isolated, temperature and humidity controlled room with a filtered air supply with 12 hour cycled light. Animals were fasted 6 hours prior to dosing. Each pig was pre-medicated with atropine sulfate (0.5 mg/kg), ketamine HCl (20 mg/kg), xylazine (2.5 mg/kg) and aceproxazine maleate (0.2 mg/kg). Intravenous access was established cannulation of an appropriate ear vein. Each animal then received thiopental (10.0 mg/kg) and were subsequently endotracheally intubated.

Once stable, each pig received its respective dose of either dantrolene sodium or free acid in a dose escalating fashion. Initial dose of 1.0 mg/kg iv was administered, followed every two minutes by repetitive 0.5 mg/kg bolus doses with the exception of one pig that received additive bolus doses achieving a cumulative dose of 10.5 mg/kg. Muscle responsiveness to the relaxant effects of dantrolene was monitored via train of four (TOF) of the forelimb using a TOF Guard. The stimulus was delivered at 20 millivolts at 0.5 second intervals. Train of four was monitored for each dose level until muscle contraction was no longer evident in response to stimuli. At the conclusion of the study, each pig was euthanized while anesthetized with intravenously delivered sodium pentobarbital solution.

Data from this study was analyzed. The relative ED 95 for each the sodium and free acid formulation was determined to be 2.5 mg/kg as a weight based dose and advanced for study in the MHS swine as set forth in Example 7.

Example 7

In this study of the effects of two low volume, high concentration colloidal dantrolene formulations in the treatment of halothane/succinylcholine induced Malignant Hyperthermia in swine, nine swine that were shown by DNA analysis to be homozygous for the halothane sensitive allele (i.e., the 11 genotype) were studied. On the initial day of the study period, pigs were randomly assigned to the following groups:

| Group | Test Article | Dose mg/kg | Dose Conc. mg/mL | No. of Animals (maximum) |
| --- | --- | --- | --- | --- |
| Control | 0.9% saline | 0 | 0 | 3 |
| DFA | (dantrolene free acid) | 2.5 | 40 | 3 |
| DS | (dantrolene sodium) | 2.5 | 50 | 3 |

Each of the pigs was anesthetized with IM injections of atropine sulfate (0.05 mg/kg), ketamine HCl (20 mg/kg), xylazine HCl (2.5 mg/kg) and acepromazine maleate (0.2 mg/kg). Sodium thiopental (10 mg/kg) and intravenous fluids (0.9% saline; approximately 4.0 mL/kg/hr) were administered via a catheter into an ear vein. Animals were endotracheally intubated and artificial ventilation was initiated. Endotracheally intubated animals were ventilated to ensure adequate oxygenation. The anesthetized animals were monitored for end tidal carbon dioxide (ETCO2), intra-arterial blood pressures, peripheral oxygen saturation (SpO2), electrocardiograms, and core body temperature.

Following stabilization, administration of halothane 2% (approximately 2MAC) was initiated. After approximately 15 minutes of halothane administration, succinylcholine (2 mg/kg) was administered via a catheter into an ear vein. Definitive diagnosis of MH crisis was determined by the documented presence of at least two of the following parameters: ETCO2>70 torr, increased rectal temperature >3° C., arterial pH of equal to/less than 7.25 and/or significant muscular rigidity. Following documentation of the onset of MH halothane was discontinued. Pigs either received no treatment (control) or one of the test articles (DFA or DS) via intravenous administration at a dose equivalent to the ED95 (2.5 mg/kg) established in a previous study in normal pigs. Progression and/or regression of the MH crisis was evaluated at approximately 1 minute intervals for the initial 20 minutes following onset and then at 2 minute intervals until cessation (if attained). Neuromuscular blockade was monitored by measuring train of four (TOF) twitch in one of the forelimbs using a TOF Guard. The stimulus for the TOF was delivered as a train of four pulses where each pulse was 0.5 seconds apart. However, reliable measurement of TOF was not possible as the twitch response was masked by the profound muscle rigidity. Following treatment, the surviving pigs (DFA and DS) were allowed to recover from anesthesia and were euthanized at approximately 120 hours post treatment.

All of the pigs developed MH after exposure to the triggering agents, halothane and succinylcholine. Typical signs of the MH episodes included increased core temperature, hypercarbia with ETCO2>70 mm Hg, an acidotic state reflected by consistent decreases in arterial pH, significant muscular rigidity, severe tachycardia and marked hypotension. The constellation of muscular rigidity, tachycardia and hypotension result in state of hypoperfusion as evidenced by narrowing of the pulse pressure. After it was determined an MH crisis was observed, the pigs received either no treatment (control) or one of the test articles (DFA or DS). The control pigs were euthanized after it was determined that the MH episode was not naturally regressing. After treatment with DFA or DS, the MH crisis was quickly aborted in all animals. The pigs were removed from the ventilator, extubated, returned to their cages, and allowed an approximate 120 hour recovery period. Upon observation 12 to 24 hours after return to their cages, there were no signs of cognitive, neurologic, or neuromuscular dysfunction in any of the treated animals. All of the treated pigs were judged by the principal investigator to be not remarkable at the terminal sacrifice.

Example 8

The pigs in Example 7, upon observation 12 to 24 hours after return to their cages, had no signs of cognitive, neurologic, or neuromuscular function in any of the treated animals.

The phenomena of altered cognitive abilities and function as well as neuropsychiatric changes with or without impaired motor function is commonly referred to as "pumphead" among anesthesiologists, cardiothoracic surgeons, and certain other medical personnel. Pumphead is not related to MH. However, the inventors note that patients with MH have an altered blood flow where the flow rate is not zero, but is significantly different from normal. For altered blood flow that represents a reduction in pressure, this is considered to be greater than a 10% decrease from baseline systolic pressure, or associated decrease in mean arterial pressure, but less than a 95% decrease. Pulsatile changes or temporary elevations in blood pressure are also considered to be altered blood flow. In view of the observed results, the inventors envision that the prophylactic administration of dantrolene, or one of its salts, analogs or relatives, preferably in low volume, high concentration form as described in Example 7 or, alternatively, in the normal form commonly used in the clinic and described in the Professional Product Labeling for Dantrium® Intravenous (P&G Pharmaceuticals), should prevent or limit the effects of pumphead. While not being bound by theory, dantrolene may prophylactically address neurological complications of pumphead via a unique and synergistic combination of a number of intracellular and/or metabolic mechanisms, which work in concert for the stabilization of intracellular calcium and other concomitant actions. Dantrolene should also be suitable as a treatment capable of minimizing neurological complications when provided in a manner timely to an insult.

Cardiothoracic surgeons have, for many years, been performing open heart surgeries for blocked coronary arteries, valve reconstruction, repair of aortic arches and aneurysms, as well as other operations requiring cardiopulmonary bypass. While successful surgical outcomes are common place, so too are the deficits of memory, concentration, attention, and affect that accompany procedures requiring cardiopulmonary bypass. The incidence of the neurocognitive deficits is quite high. Published reports reveal that just over 50% of all CPB patients experience some form of cognitive deficit following surgery. A total of almost 35% of post-bypass patients continue to exhibit deficits at 6 weeks, and 24% suffer from deficits at one year post-bypass. The reported incidence of neurocognitive deficit attributed to CPB is approximately 54% at 5 years post-bypass. The exact nature and etiology of neurocognitive deficits associated with CPB is not completely understood, but has been well studied in a number of controlled prospective studies.

Neurocognitive deficit induced from iatrogenic insult, such as in the case of "pumphead" arising from cardiopulmonary bypass, or traumatic incidents reflects a complex and multifaceted injury. Some researchers have suggested that neuronal injury can occur in response to vague conditions such as hypoxia, ischemia, insufficient glucose levels, or inappropriate blood pressures or insufficient flow rates or pulsatile pressures. Individually, a description can be proposed for the cause and effect for various factors and their potential relationship to neuronal injury or neuronal death. For example, it is known as fact that a given mass of "cool" cerebral tissue has a lower energy demand and, hence, consumes less oxygen and glucose than the same given mass at body temperature. It is also true that one principle reason for cooling cerebral tissue while on cardiopulmonary bypass is to decrease the metabolic demands of this tissue. The concept is that cool tissue will better survive the sub-optimal supply of blood, oxygen, glucose and other nutrients as well as the decreased ability to metabolize and eliminate physiologic waste products while on CPB. Further, it is likely to be true that upon re-warming from a cooled "neuroprotective" state, the physiologic requirements of individual cells may well exceed the supply of oxygen and nutrients than can be delivered under the normal flows of CPB. These, however, do not elucidate the underlying mechanism behind the resulting neurocognitive deficit (pumphead), nor reveal the best method of treatment.

Other researchers have implicated specific ion channels or receptors; such as NMDA, non-NMDA ionotropic, sodium channels, calcium channels and others as potential causes for neuronal injury or death. Still others have cited the presence or deposition of substances such as glycine, glutamine, glutamic acid, kainic acid, and others as possible toxic agents.

An array of potential receptor-mediated biochemical mechanisms have been discussed in the literature as possible explanations for the central origins of pumphead. Essentially, each of the various schools of thought has had its favored mechanism, usually centered around a particular receptor— or even a particular subunit of a particular receptor, as in the case of Chenard, U.S. Patent Application Pub. No. 2002/ 0072485 and others by Chenard, or Kozachuk, U.S. Patent Application Pub. No. 2003/0045450.

Thus, one school of thought has focused on N-methyl-D-aspartate (NMDA) receptors, which can mediate flow of calcium ions into the cell from the extracellular space. This school of thought, typified by the Chenard application, holds that an effective means of protecting against neurological damage from impairment of glucose and/or oxygen supply to the brain is simply to treat with an NMDA antagonist, of proper subunit selectivity. However, it is a fairly easy matter to find reasons why such a simplistic approach might be doomed to failure, reasons that include the theory of calcium-induced calcium release (CICR), which holds that even a relatively minor increase in intracellular calcium ions can trigger the release of calcium from the endoplasmic reticulum. See for example Makarewiez et al., J. Neurochem., 85(suppl. 2):20. The current inventors recognize this as a consequence of an intact ryanodine receptor mechanism, which provides an ample intracellular source—the ER—for calcium ions, either in the face of incomplete blockage of the NMDA-R mechanism or of other pathways to calcium ion influx. In short, in view of the CICR mechanism, nearly complete blockage of the NMDA-R mechanism would be required to prevent triggering of intracellular calcium ion release, and even if complete blockage were accomplished, other pathways for calcium-induced calcium release from intracellular stores would need to be blocked in any case.

Another school of thought focuses on glutamate receptors that are non-NMDA receptors but which can also mediate flow of calcium ions into the cell. See for example Bokesch, Am. Soc. Anesth. Newsletter, 1996, vol. 60 (8). In the context of the aforementioned, CICR, this quite likely represents another parallel mechanism for triggering of calcium release, which cannot be blocked through NMDA-R antagonism.

Yet another school of thought focuses on the kainic acid (KA) mediated mechanisms, in the context of apoptosis of neuronal cells. Thus, kainic-induced neurological damage was prevented by alpha-amino-3-hydroxy-5-methylisoxazole-4-proprionic acid (AMPA) receptor antagonist CNQX, but not by the NMDA receptor antagonist MK801, nor by the membrane L-type calcium channel antagonist nifedipine. See Li S Y, Ni J H, Xu D S, and Jia H T, Neurosci Lett. 2003 Dec. 4; 352(2):105-8. In other words, in contrast with the NMDA school of thought, these authors found evidence of a calcium ion-related mechanism of neuronal damage that is not treatable by simply applying an NMDA antagonist.

Currently, drugs are under development that target every step in the cascade of events contributing to neuronal damage and cognitive loss. These include glutamate-release inhibitors, NMDA receptor antagonists, sodium and calcium channel blockers, free radical scavengers, apoptosis inhibitors and others. What does not seem to have been recognized and focused upon is the multiplicity of mechanisms by which neuronal damage and cognitive loss can occur with altered blood flow and changes in body or tissue temperature—even under the umbrella of Ca2+ mediated mechanisms—and thus the conclusion that a number of these mechanisms must be blocked in concert has not been recognized, nor has the requisite pharmacological intervention been elucidated in light of this conclusion. In particular, what also does not seem to have been recognized is the significant therapeutic potential of dantrolene and its simultaneous pharmacologic activities against a number of these mechanisms. The current invention emphasizes that pharmaceutical-based prophylaxis and treatment of "pumphead" and related injuries should have dantrolene as the primary modulator of intracellular calcium; although combinations of dantrolene with other agents are within the scope of the invention, using anything other than dantrolene (or a salt, analogue or relative thereof, which is a ryanodine receptor antagonist) will, broadly, lower the therapeutic index and/or result in sub-optimal prevention or treatment.

That dantrolene blocks the release of intracellular calcium stores from the endoplasmic reticulum is well understood. However, in separate publications from distinct groups, dantrolene has been shown to be an effective inhibitor, either directly or indirectly, of at least three additional mechanisms affecting neuronal damage and cognitive function. Evidence from cell culture studies by Frandsen and A Schousboe (Journal of Neurochemistry, Vol 60, 1202-1211) shows that dantrolene inhibits the toxicity induced by both glutamate and NMDA. Also in cell culture, Frandsen and Schousboe also showed that the toxicity of quisqualate (QA), which stimulates Ca2+ release from an intracellular store that is independent of Ca2+ influx, is also inhibited by dantrolene. Moreover, a 2002 publication from Romanian researchers (Popescu et al., J. Cell. Mol. Med. 6(4):555) showed that dantrolene inhibits the kainic acid-mediated apoptosis mechanism.

The current inventors recognized for the first time that dantrolene administration provides at least four synergistic protective actions in the context of altered blood flow scenarios which are simultaneously required for neuroprotection in the case of cardiopulmonary bypass and against other iatrogenic cerebrospinal disturbances. Thus, the current inventors have recognized that neurocognitive and motor deficits which are experienced by some patients after anesthetics and operations utilizing extracorporeal circulation, such as CPB, or in case where induced hypotension or hypothermia is performed, are the result of a constellation of factors, with no one event or factor being singularly dominant as the causative factor, and yet dantrolene has the unique ability to treat multiple mechanisms in such a way as to provide broad protection in these circumstances.

Conclusions drawn from studies of the peripheral nervous system, or from cranial nerves such as the optic nerve, are broadly of questionable value in matters of pumphead, and of cerebrospinal tissues in general. Underscoring this is the fact that surgical patients with a medical history that includes stroke are no more likely to suffer from pumphead than those with no stroke history. See Warner, Int. Anesth. Res. Soc. 2004 Review Course Lectures, presented at the 78th Clinical and Scientific Congress, Tampa, Fla., p. 123. One basis for understanding this lies in the physiology of the cranial nerves as contrasted with the cerebrospinal nervous tissue.

In particular, the twelve paired cranial nerves, with the exception of CN I (olfactory) and II (optic), originate in the brainstem; which is comprised of the midbrain, pons, and medulla oblongata. Cranial nerves are generally categorized as being sensory, motor or mixed (both sensory and motor). Cranial nerves originate at nuclei located on the brainstem, with sensory nuclei located laterally and motor and mixed nuclei more centrally located. The sensory nuclei receive their sensory input from the periphery, but the sensory receptor cell bodies are never in the nucleus itself. Rather, they are located just outside the CNS in ganglion.

Cranial nerves, as PNS components, tend to be accompanied by a dedicated arterial blood supply that, via smaller perforating arteries, provide blood flow throughout its length. Typically, cranial nerves lack any significant source of collateral blood flow. As an Example, the optic nerve has an average diameter of 1.5 mm and has an intra-orbital length of about 30 mm and maintains a dedicated vessel throughout its entire length. The ophthalmic artery arises from the distal end of the internal carotid artery and travels with the optic nerve toward the posterior aspect of the eye. The posterior third of the optic nerve is supplied by vessels arising from the anterior communicating and anterior cerebellar arteries, while the anterior two thirds of the nerve is supplied by the central retinal artery. Occlusion of this arterial conduit will result in a decrease or total cessation of blood flow to the tissues of this organ, including the neural cells. A specific Example of the effects of such an ischemic event is evidenced in the condition known as amaurosis fugax. Here, the central retinal artery is partially or totally occluded by an embolus (or emboli) resulting in transient (or longer lasting) monocular blindness or other disturbances of visual field recognition.

In contrast to cranial nerves, the many sensory and motor tracts of the spinal cord tend to receive their blood supply via multiple vessels with abundant collateral circulation. Throughout the cervical and thoracic regions, the spinal cord receives the bulk of its blood flow via a single anterior spinal artery and two posterior spinal arteries as well as collateral supply from branches from the intercostal arteries and the descending thoracic and lumbar aorta. The nature of the blood supply to the spinal cord minimizes the likelihood of ischemia from episodic embolic phenomena.

In instances of trauma with cord and arterial compression, or in cases such as surgical aortic cross clamp during aneurismal repair, insufficient blood flow to the cerebro-spinal cord can occur and lead to certain neurologic insults. This is especially evident in operations during which blood flow to the lower third of the cord via the artery of Adamkiewicz (arteria radiculris magna) is compromised. The incidence of transient post-operative deficits and post-operative paraplegia are reported to be 11% and 6% respectively. Higher rates are reported as cross-clamp time exceeds 30 minutes. The classic deficit is that of an anterior spinal artery syndrome with loss of motor function and "pinprick" sensation, with preservation of proprioception and vibration sensation.

The role and relationship of non-normothermic states of body temperature to the above is important. Altered states of temperature are easily induced by medical practitioners. Non-normothermic states of hypothermia can be readily induced under general anesthesia both intentionally, as in cardiopulmonary bypass, or unintentionally, where appropriate safeguards are not employed to guard against the loss of body heat.

A number of potential complications are associated with unintentional intraoperative hypothermia including altered clotting function with increased blood loss, increased frequency of infection and myocardial stress. As such, the routine practice of anesthesia has largely evolved to practice the maintenance of normothermia during most operative procedures.

Little evidence exists today to show that intraoperative hypothermia improves outcome except in the instance of deep hypothermia for circulatory arrest while undergoing cardiopulmonary bypass. Complete circulatory arrest for periods of up to one hour at core temperatures ranging from 16 degrees to 18 degrees C. offers some protection for the adult brain; where patients are expected to recover neurologically, but not necessarily neurocognitively, intact. Otherwise, mild and moderate hypothermic conditions where temperatures typically range form 32 degrees C. to 34 degrees C. have been evaluated in a number of randomized trials during CPB and have shown little, if any benefit to the patient. The issue of employing mild to moderate hypothermia during CPB as a neuroprotective technique is difficult to assess because it requires not only reducing core temperatures but rapid re-warming cycles that usually delivers hyperthermic blood to the cerebrospinal system, which may negate any potential benefit that hypothermia may have provided Mild to moderate hypothermia has been evaluated in a large prospective randomized trial as a potential therapeutic maneuver to treat patients with traumatic brain injury while in the Intensive Care Unit. In this study, no benefit was attributed to hypothermia and, in fact, elderly patients suffered a greater rate of complications when randomly assigned to the hypothermic group.

The non-normothermic state of hyperthermia is a common sequellae of acute brain injury. Animal studies have shown that temperatures ranging from as little as 1 degree C. from normal, while either during or after various forms of acute brain injury markedly worsen neurologic outcome. The presence of hyperthermia has been regarded as a reliable prognostic indicator of poor neurological and neurocognitive outcome in acute brain injury. We know of no proposed advantages, theoretical or otherwise, linking hyperthermia to improved neurological or neurocognitive outcomes.

Regarding NMDA and non-NMDA receptors, it is likely that the act of either cooling, re-warming, or the cyclic combination of both cooling and re-warming of the cerebrospinal system results in the expression of these potentially destructive receptor mechanisms. It is also likely that the temperature flux causes an imbalance of nutrient substrates such as oxygen and glucose out of balance to the specific needs of the cerebrospinal system as any given moment in the course of the cooling and re-warming procedure.

The application of a single, safe agent, namely dantrolene or one of its salts or relatives, for the prevention and treatment of neurological and cognitive damage in CPB and related insults has fundamental advantages over combination approaches that could be envisioned. To begin with, the safety record and therapeutic index of dantrolene sodium are extremely favorable. In the context of this patent, we define "therapeutic index" of a therapeutic drug (or mixture) to be the quotient A/B, where A and B are defined as follows: A is the LD50 (dose yielding 50% lethality) of the drug when given intraperitoneally to rats; and B is the dose of the drug that when given i.p. yields 50% reduction of apoptotic nuclei in the cortex of rats given 5 mg/kg kainic acid, according to the protocol described by Popescu et al. in [J. Cell. Mol. Med. 6(4):555 (2002)]. As the quantity A has been shown to be 780 mg/kg (Fournier, P, 1982, Dossier toxicologique, pharmacologique, pharmacocinetique du Dantrium IV. Lyon, Laboratorie Obercal), and the value of B is 10 mg/kg according to the Popescu paper cited above, the therapeutic index for dantrolene as defined herein is calculated to be 78. A therapeutic index greater than 10, and especially greater than about 50, is viewed in the context of this invention as being of importance, particularly in the context of a surgical procedure where drug interactions are already complicated, and a large zone of comfort (at least an order of magnitude) between administered dose and lethal dose is of course highly desirable. For example, dantrolene does not cause cardiopulmonary depression even at doses as high as 7.5 mg/kg i.v. Such depression, if caused by either of the drugs in a given combination, would of course be potentially detrimental in the context of a cardiopulmonary bypass operation. This is certainly the case for suggested combinations involving local anesthetics (as sodium channel modulators), since the cardiotoxicity of the 'caines (lidocaine, bupivacaine, etc.), and the low therapeutic index, is well known. Only rarely does dantrolene cause severe cardiopulmonary complications when combined with calcium channel blockers. In contrast, the drugs to be used in the combinations described in Jensen (U.S. Patent Application Pub. No. 2003/0092730), for Example, include drugs such as topiramate (Topamax), which " . . . has a potential . . . to cause CNS depression, as well as other cognitive and/or neuropsychiatric adverse events . . . ". (2001 Physicians' Desk Reference, page 2394).

The prevention of cognitive loss—pumphead—due to CPB or related circumstance differs in many fundamental ways from the treatment of a pre-existing disease. It does not involve any known dominant heredity or other prefactor that introduces heightened risk of damage, as is the case with Malignant Hyperthermia. Since the preventive steps are to be taken in the absence of a pre-existing neurological disorder, such steps must necessarily be highly safe, in order to comply with a reasonable benefit/risk ratio. The increase in focus and certainty that comes from the diagnosis of a pre-existing condition is not present. And in the current climate of medical practice, prevention typically plays a secondary role to treatment.

The neuroprotective efficacy of a low volume/high concentration dantrolene formulation may be demonstrated using a recovery model of CPB in the rat described by Mackensen et al (Anesthesiology. 2001 December; 95(6):1485-91). For example, three groups of rats may be subjected to 60 min of normothermic (37.5 degrees C.) nonpulsatile cardiopulmonary bypass (CPB) using a roller pump and a membrane oxygenator. Group 1 rats (n=10) receive no treatment. Group 2 rats (n=10) are pretreated with low volume dantrolene IV, 2.5 mg/kg, and Group 3 rats (n=10) are pretreated with low volume dantrolene IV, 5.0 mg/kg. A fourth group, (Group 4) serve as sham operated controls (n=10). Neurologic outcome is assessed on days 1, 3, and 12 after CPB using standardized functional testing. Neurocognitive outcome, defined as the time (or latency) to finding a submerged platform in a Morris water maze (an indicator of visual-spatial learning and memory), is evaluated daily from post-CPB days 3-12. Under this investigation, the neurologic outcome should be worse in Group 1 versus the Groups 2, 3 and 4 at all three measurement intervals. Group 1 should also have longer water maze latencies compared with Groups 2, 3 and 4, indicating significant neurocognitive dysfunction after CPB. This investigation should demonstrate that dantrolene pretreatment, at both 2.5 mg/kg and 5.0 mg/kg attenuates CPB associated neurologic and neurocognitive impairment in a rodent recovery model.

The neuroprotective effect of dantrolene may be compared with that of xenon, an agent previously shown to be protective in this animal model. (Ma et al, Anesthesiology. 2003 March; 98(3):690-8) In this comparison, following surgical preparation, rats would be randomly divided into four groups of 10 rats per group: (Group 1) sham rats would be cannulated but would not undergo nonpulsatile cardiopulmonary bypass (CPB); (Group 2) CPB rats would be subjected to 60 min of CPB using a membrane oxygenator receiving a gas mixture of 30% O2, 65% N2, and 5% CO2; (Group 3) CPB+dantrolene rats receive dantrolene (10.0 mg/kg IV) 15 min prior to undergoing 60 min of CPB with the same gas mixture as Group 2; and (Group 4) CPB+xenon rats undergo 60 min of CPB using an oxygenator receiving 30% O2, 60% xenon, 5% N2, and 5% CO2. Following CPB, the rats would recover for 12 days, during which they would undergo standardized neurologic and neurocognitive testing (Morris water maze). In this investigation, the sham, CPB+dantrolene and CPB+xenon groups all would have significantly better neurologic outcome compared to the CPB group on postoperative days 1 and 3. Compared to the CPB group, the sham, CPB+dantrolene, and CPB+xenon groups would have better neurocognitive outcome on postoperative days 3 and 4. By the 12th day, the neurocognitive outcome would remain significantly better in the CPB+dantrolene and CPB+xenon groups compared to the CPB group. This investigation would show the efficacy of dantrolene (10.0 mg/kg) in attenuation of CPB-induced neurologic and neurocognitive dysfunction is comparable to xenon.

In humans the neuroprotective effect, e.g., effectiveness in preventing or reducing pumphead, could be demonstrated by an investigation where twenty patients about to undergo coronary artery re-vascularization during cardiopulmonary bypass would be randomly assigned to either a dantrolene treatment or non-treated control group. Prior to surgery, each patient would be given a battery of nine standard tests designed to measure cognitive function in four broad categories; attention and concentration; verbal memory; abstraction and visual orientation; and figure (numbers) memory. Patients would again administered the same tests 24 hours and six weeks post-operatively. Each assessment would be performed by the same investigator who would be blinded to the patient's study group assignment. At the time of the operation, each patient would be induced of general anesthesia according to a protocol utilizing a modified cardiac/narcotic technique. All agents would be administered on a weight based dose (mg/kg) whenever possible. Volatile anesthetic agents would be administered and regulated by the anesthesiologist via the endotracheal tube to maintain adequate blood and pulse pressures both pre and post bypass, and by the perfusionist during bypass to maintain pressures suitable for adequate tissue perfusion. A standardized protocol by which the operation is to be performed would be designed and applied to each patient enrolled in this study. Protocols are developed for each aspect and phase of the operation, including vena-caval/atrial cannulation; initiation and maintenance of cardiopulmonary bypass utilizing a membrane oxygenator; initiation and maintenance of cardioplegia; standardized monitoring, induction, and maintenance of cooling and re-warming procedures; and recommended procedures for preparation for separation and actual separation from cardiopulmonary bypass, including acceptable doses of inotropic/pressor agents and transfusion therapies. Patients randomized to Group 1 (dantrolene) would receive 1.0 mg/kg of 5% (50 mg/ml) colloidal dantrolene via central venous access after the patient has been successfully endotracheally intubated and stabilized of general anesthesia, and prior to sternotomy. (For purposes of this particular trial, a dose of 1.0 mg/kg is administered to each patient although doses ranging from approximately 0.1 to 10 mg/kg and above are likely to provide a neurocognitive protective effect). The entire dantrolene dose would be administered over approximately 30 seconds. In order to ensure the double blind nature of this study, either the low volume, high concentration colloidal dantrolene (5%) or a placebo control solution of comparable volume would be injected at the appropriate time by the study coordinator. The anesthesia and surgical staff would remain blinded to the treatment assignments. Upon completion of the operative procedure, patients would be treated via standard post-CPB "fast track" treatment protocols whereby they are endotracheally extubated in the operating room upon emergence or within six hours of arriving in the Cardiac Post Anesthesia Care Unit. Approximately 24 hours and 6 weeks post extubation patients would be administered the same battery of the nine standardized tests in the same order and fashion as performed pre-operatively. To reduce possible inconsistencies of interpretation, assessments at each time interval would be performed by the same blinded investigator. In such an investigation, colloidal dantrolene treated patients would exhibit significantly less neurocognitive dysfunction than untreated patients. The findings would be significant for the 24 hour post-op assessment and for the six week follow-up assessment. Furthermore, patients receiving dantrolene therapy would test significantly better than control patients in those tests designed to assess attention and concentration. Again, the results would be similar for both post-op evaluation periods. The study would demonstrate that dantrolene, 1.0 mg/kg attenuates CPB-induced neurologic and neurocognitive impairment in man.

In this patent, we put forth the use of dantrolene and its salts, analogs and relatives for the prevention of neurological and cerebrospinal injury in a number of conditions that have not previously been recognized as treatable by this medication, nor any other medication for that matter. The invention applies in relation to a number of specific factors that induce a state of low systemic blood flow or decreased cerebral perfusion pressures, and puts forth the use of dantrolene as a preventive means. These would include, but not necessarily be limited to the following examples:

1) extracorporeal oxygenation and perfusion systems commonly utilized in cardiopulmonary bypass for thoracic and coronary artery bypass grafting surgeries (CPB), as well as other enabling techniques such as deep hypothermic circulatory arrest allowing for complex reconstructive open heart procedures such as aortic arch repair/replacement in neonatal, pediatric and adult patients where minimal blood flow (approximately 90% of normal) is generated. Neurologic complications are reportedly as high as 54% in those having undergone CPB for coronary artery bypass grafting (CABG) and other related thoracic operations [Warner, op. cit.]. Neuropsychiatric alterations range from subtle to severe cognitive impairment, personality changes, delirium, memory loss, and organic brain syndromes. Some patients experience transient and/or permanent impaired motor function. Estimates of patients sustaining permanent deficits range from 2% to 50% or more. The risk of neuropsychiatric injury tends to increase as the total length of CPB time increases. Shorter periods of CPB are, however, not necessarily risk free and are also known to cause neuropsychiatric and cognitive alterations. In the instance of CABG performed without the use of extracorporeal oxygenation and perfusion (off-pump techniques), patients reportedly have experienced signs and symptoms associated with "pumphead". This is believed in part to be due to periods of controlled (induced) hypotension (decreased cardiac stoke volume and cardiac output) and/or induced bradycardia (decreased heart rate) established to create conditions suitable for coronary graft placement and suturing. The normal cardiac cycle results in systemic blood flow which is pulsatile in arterial vessels. The arterial tree continues to taper in diameter and, upon reaching the systemic capillary blood vessels in tissues and end organ beds, the pulsatile flow gradually changes to a continuous flow, also known as laminar flow. CPB establishes a decreased systemic blood pressure, decreased mean arterial pressure (MAP) as well as a decreased pulsatile waveform pattern of blood flow normally generated by the usual cardiac cycle of contraction and relaxation, which yields specific and independent systolic and diastolic pressures. While controversy continues to surround the "ideal" systemic arterial pressures to be generated by CPB and other extracorporeal oxygenation/perfusion systems (as read by radial artery arterial pressure tracing), the majority of heart centers and perfusionists typically recommend and practice generating CPB flow rates of 2.0 to 2.5 L/min/m2 (approximately 50 to 60 ml/kg/min) which will usually generate a mean arterial pressure between 50 and 80 mm Hg.

2) surgical procedures using extracorporeal intervention in blood flow other than CPB, including but not limited to extracorporeal membrane oxygenation (ECMO), states associated with the induction and maintenance of induced and/or controlled hypotension as commonly employed in neurosurgery, vascular surgery and "off-pump" coronary artery bypass grafting surgery. Dantrolene treatment and/or pretreatment is recognized in this patent as preventive in the case of other conditions, since neuropsychiatric changes, altered cognitive function, and impaired motor function are not solely related to decreased pressures and flow rates caused by CPB. Extracorporeal membrane oxygenation (ECMO) is a relatively new treatment modality which provides for a temporizing method of extracorporeal oxygenation in patients, typically neonates, whose lungs cannot withstand more conventional mechanical or assisted ventilation techniques. This particular patient population experiences an unusually high risk of cerebral, cognitive, and motor impairment.

Certain trauma conditions, especially shock and trauma associated with decreased intravascular circulating blood volumes, and particularly injuries associated with increased intracranial pressures (ICP), decreased cerebral blood flow (CBF) and altered cerebral perfusion pressures (CPP). Importantly, conditions treatable by dantrolene as per this patent include trauma to the central nervous system, especially events resulting in head injuries. In either closed or open head trauma, the brain typically sustains injury on a number of levels and in a cascading fashion. These injuries are frequently accompanied with increased intracranial pressures attributed to cerebral hemorrhagic events or to advancing cerebral edema. As intracranial pressures (ICP) increase (due to edema or hemorrhage), the autoregulated cerebral blood flow is further impaired both locally and globally. Arterial hypertension occurs as a result of inborn physiologic reflexes, which further aggravates cerebral edema and increases ICP. Cerebral perfusion pressure is defined as the difference between mean arterial pressure at the level of the brain and either the central venous pressure or the intracranial pressure, which ever is greater. It is widely recognized that this pressure should be maintained above 60 mm Hg in order to sustain adequate CPP, cerebral perfusion and cerebral blood flow. Maintaining adequate perfusion pressures may be difficult if not impossible, in the setting of many head injuries. Brain injury, especially injuries associated with compromised cerebral blood flow from altered CPP and increased ICP, is frequently associated with neurophysiologic alterations as well as impaired cognitive and motor function. It is further anticipated that due to local conditions established by reflexes similar to those described above as related to head injuries, that the long term effects of spinal cord injury may be minimized or in someway ameliorated by the administration of dantrolene, one of its salts, analogs or relatives.

The invention also applies in relation to non-normothermic temperatures resulting from induced hypothermia techniques utilized as a possible neuroprotective measure or as a function of deep circulatory arrest while on CPB as well as the re-warming periods and possible hyperthermic overcorrection, and hypothermia resulting from the poikilothermic nature of anesthetized patients, as well as episodic hyperthermia resulting from exogenous or endogenous influences, including but not limited to sepsis, hypothyroidism, hemorrhagic brain injury, overaggressive attempts to rewarm, and fulminant infection.

For "pumphead" and the related applications of focus in this Example, the currently marketed dantrolene formulations may be applicable provided that the large volumes of administration are not prohibitive, as may be the case in many clinical situations (though less commonly with field situations), and where the mannitol present in such a formulation is not strongly contraindicated. Both oral and injectable Dantrium® formulations (Procter & Gamble) can be used prophylactically, and in particular the injectable Dantrium® formulation is applicable either prophylactically or therapeutically.

It can be readily envisioned that a dantrolene salt, in a pharmaceutically acceptable formulation, can be administered as prophylactic treatment by skilled practitioners, prior to inducing an altered physical or physiologic state via some form of medical or surgical intervention known to compromise, or in some way potentially jeopardize, the baseline neuropsychiatric state and cognitive function of any one individual. Furthermore, it is also expected that treatment with such a formulation would yield benefit in the treatment of alterations in neuropsychiatric or altered cognitive abilities when treatment is initiated in a timely fashion, when deficits may be attributed to any number of factors as mentioned above.

It is anticipated that a wide range of doses of this dantrolene sodium formulation will obtain the intended effect, particularly in view of the high therapeutic index of dantrolene. A lower volume formulation as provided herein will allow for easier and more accurate administration in a more rapid manner.

It is expected that doses ranging from 0.1 to 10.0 mg/kg in single or divided multiple doses will prove efficacious, depending upon the age, pre-existing state of health, and possible extent of neurologic injury, and depending upon the type and extent of the insult. The preferred range is about 0.5 to about 4 mg/kg, as a single, total dose. Multiple doses or extended dosing schedules may be employed depending upon the nature or duration of the underlying physiologic insult.

In addition to dantrolene salts, other agents may provide similar protection against neuropsychiatric changes and cognitive impairment, particularly in cases where the agent has similar pharmacologic action as dantrolene sodium, and especially if it is known to provide relief from MH. Thus, a pharmacologically active relative of dantrolene, such as a compound containing a hydantoin group and/or a nitrophenyl or nitrofuranyl group, which affects the ryanidine receptor and through it intracellular calcium release, would be expected to be active within the present invention, particularly if it diminishes the symptoms of MH. As an instructive example, while certain analogues such as azumolene are pharmacologically related to dantrolene and may be of use in the present invention, dantrolene would be preferred over azumolene because the latter has been shown to be of limited benefit in the treatment of Malignant Hyperthermia (MH); in contrast, dantrolene sodium is the most efficacious rescue agent known for MH. It is also anticipated that new dantrolene analogs and chemical relatives will become available, and to the extent that such a new agent has similar pharmacologic actions, and especially to the extent that it relieves the symptoms of MH, it is to be expected that the same agent can be used in the context of the present invention.

The present invention also provides dantrolene sodium in a pharmaceutically acceptable formulation that can deliver the requisite amount of drug in a liquid volume that is one or, in some embodiments, two orders of magnitude less than that required by the current Dantrium® formulation (which requires volumes on the order of one-half to one liter for a human application), and which therefore minimizes or circumvents the complications and dangers associated with large liquid volumes of administration, particularly for the treatment of the conditions of focus in this patent, including but not limited to malignant hyperthermia and pumphead. This substantial reduction in volume and associated problems is not foreseen in the Mangat et al. patent, but should be considered of high importance in view of, for example, the added complications imposed on the surgical team when a liter of aqueous solution must be administered in a procedure whose success is dependent on critical control of an extracorporeal circuit. Furthermore, the sheer time required to reconstitute several dozen vials of the currently marketed I.V. dantrolene formulation can have severe repercussions in the attempted treatment of many of the CNS disturbances of focus herein, particularly emergency situations. With certain embodiments of the current invention, a dantrolene dose of up to 500 mg can be delivered in liquid volumes less than 50 ml in all cases; a 300 mg dose can be delivered in a volume of less than 30 ml, more preferably less than 10 ml, and most preferably less than or equal to about 5 ml. The latter volume is sufficiently small that the entire formulation could be loaded into an auto injector in accordance with standard volumes of such devices.

Certain embodiments of this invention, exemplified but not limited to the Examples herein, provide low-volume dantrolene sodium formulations that are either a solution, or contain particles that are sufficiently small to permit safe intravenous injection, in particular such that over 95% of the particles are less than 0.8 microns, or preferably less than 0.45 microns (viz., such that they can pass through a standard 0.45 micron filter). Other routes, such as intramuscular, intrathecal, intraocular, extracorporeal, etc. are also made possible by these low volumes of administration.

Low-volume formulations of dantrolene and its salts can be prepared in a number of ways. The pharmaceutically acceptable solvent N,N-dimethylacetamide, together with hydroxyl-containing solvent(s), provide for a powerful solubilization matrix, and this can be modulated with polyethylene glycol (PEG), and appropriate modifiers such as base and surfactant. Alternatively, small particles of solid dantrolene or one of its salts can be dispersed by homogenization techniques, for example, as described in Examples 1, 3 and 4.

What is claimed is:

1. A method for treating hyperthermia in mammal, comprising the step of:
   administering to a mammal in need of treatment for hyperthermia a therapeutically effective amount of a safe for injection, low volume liquid formulation of dantrolene sodium comprising:
   dantrolene sodium at a concentration in the range of 3.33 mg/ml to 166.67 mg/ml;
   a water-soluble polysorbate;
   a compound selected from the group consisting of sorbitol and mannitol; and
   water as a liquid carrier,
   wherein said dantrolene sodium and water are present together as a colloidal dispersion of dantrolene sodium particles in the water,
   wherein the dantrolene sodium particles are less than about 2 microns in average diameter, and
   wherein the formulation is safe for intravenous administration.

2. The method of claim 1, wherein the formulation comprises dantrolene sodium at a concentration in the range of 30-80 mg/ml or in the range of 10-60 mg/ml.

3. The method of claim 1, wherein the dantrolene sodium is the primary modulator of intracellular calcium present in the formulation.

4. The method of claim 1, wherein the formulation consists essentially of:
   dantrolene sodium at a concentration in the range of 3.33 mg/ml to 166.67 mg/ml;
   a water-soluble polysorbate;
   a compound selected from the group consisting of sorbitol and mannitol; and
   water as a liquid carrier,
   wherein said dantrolene sodium and water are present together as a colloidal dispersion of dantrolene sodium particles in the water,
   wherein the dantrolene sodium particles are less than about 2 microns in average diameter, and
   wherein the formulation is safe for intravenous administration.

5. The method of claim 1, wherein the formulation further comprises polyvinylpyrrolidone (PVP).

6. The method of claim 5, wherein the formulation consists essentially of:
   dantrolene sodium at a concentration in the range of 3.33 mg/ml to 166.67 mg/ml;
   a water-soluble polysorbate;
   a compound selected from the group consisting of sorbitol and mannitol;
   polyvinylpyrrolidone (PVP); and
   water as a liquid carrier, wherein said dantrolene sodium and water are present together as a colloidal dispersion of dantrolene sodium particles in the water, wherein the dantrolene sodium particles are less than about 2 microns in average diameter, and wherein the formulation is safe for intravenous administration.

7. The method of claim 1, wherein the administering step further comprises administering a quantity of 3-150 milliliters of the formulation to the mammal.

8. The method of claim 7, wherein the quantity is 10 milliliters or less.

9. The method of claim 8, wherein the quantity is 5 milliliters or less.

10. The method of claim 1, wherein the administering step further comprises administering a dose of 250-300 mg dantrolene sodium to the mammal.

11. The method of claim 7, wherein the administering step further comprises administering a dose of 250-300 mg dantrolene sodium to the mammal.

12. The method of claim 1, further comprising a step of:
preparing the safe for injection, low volume liquid formulation of dantrolene sodium by combining a dry formulation comprising:
  dantrolene sodium consisting essentially of dantrolene sodium particles less than about 2 microns in average diameter;
  a compound selected from the group consisting of sorbitol and mannitol; and
  a water-soluble polysorbate;
  said dry formulation being reconstitutable by water to provide a colloidal dispersion of dantrolene sodium particles less than about 2 microns in average diameter in the water that is safe for intravenous administration,
with water to form a liquid formulation that is a colloidal dispersion of dantrolene sodium particles less than about 2 microns in average diameter in the water that is safe for intravenous administration, and in which the dantrolene sodium is present at a concentration in the range of 3.33 mg/ml to 166.67 mg/ml,
and whereupon said combining, the liquid formulation is ready for injection.

13. The method of claim 12, wherein said combining comprises mechanical agitation.

14. The method of claim 13, wherein said combining is performed in one minute or less.

15. A method for treating malignant hyperthermia in a mammal, comprising the step of:
administering to a mammal in need of treatment for malignant hyperthermia a therapeutically effective amount of a safe for injection, low volume liquid formulation of dantrolene sodium comprising:
dantrolene sodium at a concentration in the range of 3.33 mg/ml to 166.67 mg/ml;
a water-soluble polysorbate;
a compound selected from the group consisting of sorbitol and mannitol; and
water as a liquid carrier,
wherein said dantrolene sodium and water are present together as a colloidal dispersion of dantrolene sodium particles in the water,
wherein the dantrolene sodium particles are less than about 2 microns in average diameter, and
wherein the formulation is safe for intravenous administration.

16. The method of claim 15, wherein the formulation comprises dantrolene sodium at a concentration in the range of 30-80 mg/ml or in the range of 10-60 mg/ml.

17. The method of claim 15, wherein the formulation comprises dantrolene sodium at a concentration in the range of 30-80 mg/ml or in the range of 10-60 mg/ml.

18. The method of claim 15, further comprising a step of:
preparing the safe for injection, low volume liquid formulation of dantrolene sodium by combining a dry formulation comprising:
  dantrolene sodium consisting essentially of dantrolene sodium particles less than about 2 microns in average diameter; and
  a compound selected from the group consisting of sorbitol and mannitol; and
  a water-soluble polysorbate;
  said dry formulation being reconstitutable by water to provide a colloidal dispersion of dantrolene sodium particles less than about 2 microns in average diameter in the water that is safe for intravenous administration,
with water to form a liquid formulation that is a colloidal dispersion of dantrolene sodium particles less than about 2 microns in average diameter in the water that is safe for intravenous administration, and in which the dantrolene sodium is present at a concentration in the range of 3.33 mg/ml to 166.67 mg/ml,
and whereupon said combining, the liquid formulation is ready for injection.

19. The method of claim 18, wherein the dry formulation further comprises polyvinylpyrrolidone (PVP).

* * * * *